(12) United States Patent
Wondka et al.

(10) Patent No.: US 8,770,193 B2
(45) Date of Patent: Jul. 8, 2014

(54) METHODS AND DEVICES FOR SENSING RESPIRATION AND CONTROLLING VENTILATOR FUNCTIONS

(75) Inventors: Anthony D. Wondka, Thousand Oaks, CA (US); Robert F. Bryan, San Ramon, CA (US); Lutz Freitag, Hemer (DE); Mark McCall, Berkeley, CA (US); Cuong Q. Tran, Danville, CA (US)

(73) Assignee: Breathe Technologies, Inc., Irvine, CA (US)

( * ) Notice: Subject to any disclaimer, the term of this patent is extended or adjusted under 35 U.S.C. 154(b) by 787 days.

(21) Appl. No.: 12/988,469

(22) PCT Filed: Apr. 17, 2009

(86) PCT No.: PCT/US2009/041034
§ 371 (c)(1),
(2), (4) Date: May 6, 2011

(87) PCT Pub. No.: WO2009/129506
PCT Pub. Date: Oct. 22, 2009

(65) Prior Publication Data
US 2011/0259327 A1    Oct. 27, 2011

Related U.S. Application Data

(60) Provisional application No. 61/071,251, filed on Apr. 18, 2008.

(51) Int. Cl.
*A61M 11/00*    (2006.01)
(52) U.S. Cl.
USPC .................................. 128/204.23; 128/204.21

(58) Field of Classification Search
USPC .............. 128/204.23, 207.14, 204.18, 204.21
See application file for complete search history.

(56) References Cited

U.S. PATENT DOCUMENTS

| | | |
|---|---|---|
| 50,641 A | 10/1865 | Stone |
| 428,592 A | 5/1890 | Chapman |
| 697,181 A | 4/1902 | Smith |
| 718,785 A | 1/1903 | McNary |
| 853,439 A | 5/1907 | Clark |
| 859,156 A | 7/1907 | Warnken |
| 909,002 A | 1/1909 | Lambert |

(Continued)

FOREIGN PATENT DOCUMENTS

| | | |
|---|---|---|
| DE | 19626924 | 1/1998 |
| DE | 29902267 U1 | 7/1999 |

(Continued)

OTHER PUBLICATIONS

In the U.S. Patent and Trademark Office, Supplemental Notice of Allowance dated in re: U.S. Appl. No. 10/771,803, dated Dec. 2, 2008, 2 pages.

(Continued)

*Primary Examiner* — Steven Douglas
(74) *Attorney, Agent, or Firm* — Stetina Brunda Garred & Brucker

(57) ABSTRACT

Improved methods and devices are described for sensing the respiration pattern of a patient and controlling ventilator functions, particularly for use in an open ventilation system. An apparatus for sensing respiration and synchronizing a ventilator to the respiration of a patient is described. The apparatus may include a plurality of thermal breath sensors. At least one of the plurality of thermal breath sensors may be a heated thermal breath sensor.

6 Claims, 15 Drawing Sheets

(56) References Cited

U.S. PATENT DOCUMENTS

| | | |
|---|---|---|
| 1,125,542 A | 1/1915 | Humphries |
| 1,129,619 A | 2/1915 | Zapf |
| 1,331,297 A | 2/1920 | Walker |
| 2,178,800 A | 11/1939 | Lombard |
| 2,259,817 A | 10/1941 | Hawkins |
| 2,552,595 A | 5/1951 | Seeler |
| 2,663,297 A | 12/1953 | Turnberg |
| 2,693,800 A | 11/1954 | Caldwell |
| 2,735,432 A | 2/1956 | Hudson |
| 2,792,000 A | 5/1957 | Richardson |
| 2,843,122 A | 7/1958 | Hudson |
| 2,859,748 A | 11/1958 | Hudson |
| 2,931,358 A | 4/1960 | Sheridan |
| 2,947,938 A | 8/1960 | Bennett |
| 3,172,407 A | 3/1965 | Von Pechmann |
| 3,267,935 A | 8/1966 | Andreasen et al. |
| 3,319,627 A | 5/1967 | Windsor |
| 3,357,424 A | 12/1967 | Schreiber |
| 3,357,427 A | 12/1967 | Wittke et al. |
| 3,357,428 A | 12/1967 | Carlson |
| 3,437,274 A | 4/1969 | Apri |
| 3,460,533 A | 8/1969 | Riú Plá |
| 3,493,703 A | 2/1970 | Finan |
| 3,513,844 A | 5/1970 | Smith |
| 3,610,247 A | 10/1971 | Jackson |
| 3,625,206 A | 12/1971 | Charnley |
| 3,625,207 A | 12/1971 | Agnew |
| 3,631,438 A | 12/1971 | Lewin |
| 3,643,660 A | 2/1972 | Hudson et al. |
| 3,657,740 A | 4/1972 | Cialone |
| 3,682,171 A | 8/1972 | Dali et al. |
| 3,721,233 A | 3/1973 | Montgomery et al. |
| 3,726,275 A | 4/1973 | Jackson et al. |
| 3,727,606 A | 4/1973 | Sielaff |
| 3,733,008 A | 5/1973 | Churchill et al. |
| 3,741,208 A | 6/1973 | Jonsson et al. |
| 3,754,552 A | 8/1973 | King |
| 3,794,026 A | 2/1974 | Jacobs |
| 3,794,072 A | 2/1974 | Diedrich et al. |
| 3,802,431 A | 4/1974 | Farr |
| 3,831,596 A | 8/1974 | Cavallo |
| 3,881,480 A | 5/1975 | Lafourcade |
| 3,896,800 A | 7/1975 | Cibulka |
| 3,903,881 A | 9/1975 | Weigl |
| 3,905,362 A | 9/1975 | Eyrick et al. |
| 3,949,749 A | 4/1976 | Stewart |
| 3,951,143 A | 4/1976 | Kitrilakis et al. |
| 3,961,627 A | 6/1976 | Ernst et al. |
| 3,972,327 A | 8/1976 | Ernst et al. |
| 3,985,131 A | 10/1976 | Buck et al. |
| 3,991,790 A | 11/1976 | Russell |
| 4,003,377 A | 1/1977 | Dahl |
| 4,036,253 A | 7/1977 | Fegan et al. |
| 4,054,133 A | 10/1977 | Myers |
| 4,067,328 A | 1/1978 | Manley |
| 4,106,505 A | 8/1978 | Salter et al. |
| 4,146,885 A | 3/1979 | Lawson, Jr. |
| 4,206,754 A | 6/1980 | Cox et al. |
| 4,211,086 A | 7/1980 | Leonard et al. |
| 4,216,769 A | 8/1980 | Grimes |
| 4,231,363 A | 11/1980 | Grimes |
| 4,231,365 A | 11/1980 | Scarberry |
| 4,256,101 A | 3/1981 | Ellestad |
| 4,261,355 A | 4/1981 | Glazener |
| 4,263,908 A | 4/1981 | Mizerak |
| 4,265,237 A | 5/1981 | Schwanbom et al. |
| 4,266,540 A | 5/1981 | Panzik et al. |
| 4,273,124 A | 6/1981 | Zimmerman |
| 4,274,162 A | 6/1981 | Joy et al. |
| 4,278,082 A | 7/1981 | Blackmer |
| 4,282,869 A | 8/1981 | Zidulka |
| 4,306,567 A | 12/1981 | Krasner |
| 4,323,064 A | 4/1982 | Hoenig et al. |
| 4,354,488 A | 10/1982 | Bartos |
| 4,365,636 A | 12/1982 | Barker |
| 4,367,735 A | 1/1983 | Dali |
| 4,377,162 A | 3/1983 | Staver |
| 4,393,869 A | 7/1983 | Boyarsky et al. |
| 4,406,283 A | 9/1983 | Bir |
| 4,411,267 A | 10/1983 | Heyman |
| 4,413,514 A | 11/1983 | Bowman |
| 4,421,113 A | 12/1983 | Gedeon et al. |
| 4,422,456 A | 12/1983 | Tiep |
| 4,449,523 A | 5/1984 | Szachowicz et al. |
| 4,454,880 A | 6/1984 | Muto et al. |
| 4,462,398 A | 7/1984 | Durkan et al. |
| 4,469,097 A | 9/1984 | Kelman |
| 4,481,944 A | 11/1984 | Bunnell |
| 4,488,548 A | 12/1984 | Agdanowski |
| 4,495,946 A | 1/1985 | Lemer |
| 4,506,666 A | 3/1985 | Durkan |
| 4,506,667 A | 3/1985 | Ansite |
| 4,519,387 A | 5/1985 | Durkan et al. |
| 4,520,812 A | 6/1985 | Freitag et al. |
| 4,527,557 A | 7/1985 | DeVries et al. |
| 4,535,766 A | 8/1985 | Baum |
| 4,537,188 A | 8/1985 | Phuc |
| 4,539,984 A | 9/1985 | Kiszel et al. |
| 4,548,590 A | 10/1985 | Green |
| 4,559,940 A | 12/1985 | McGinnis |
| 4,570,631 A | 2/1986 | Durkan |
| 4,571,741 A | 2/1986 | Guillaumot |
| 4,584,996 A | 4/1986 | Blum |
| 4,590,951 A | 5/1986 | O'Connor |
| 4,592,349 A | 6/1986 | Bird |
| 4,621,632 A | 11/1986 | Bartels et al. |
| 4,630,606 A | 12/1986 | Weerda et al. |
| 4,630,614 A | 12/1986 | Atlas |
| 4,644,947 A | 2/1987 | Whitwam et al. |
| 4,648,395 A | 3/1987 | Sato et al. |
| 4,648,398 A | 3/1987 | Agdanowski et al. |
| 4,658,832 A | 4/1987 | Brugnoli |
| 4,660,555 A | 4/1987 | Payton |
| 4,682,591 A | 7/1987 | Jones |
| 4,684,398 A | 8/1987 | Dunbar et al. |
| 4,686,974 A | 8/1987 | Sato et al. |
| 4,686,975 A | 8/1987 | Naimon et al. |
| 4,688,961 A | 8/1987 | Shioda et al. |
| 4,705,034 A | 11/1987 | Perkins |
| 4,744,356 A | 5/1988 | Greenwood |
| 4,747,403 A | 5/1988 | Gluck et al. |
| 4,753,233 A | 6/1988 | Grimes |
| 4,773,411 A | 9/1988 | Downs |
| 4,776,333 A | 10/1988 | Miyamae |
| 4,782,832 A | 11/1988 | Trimble et al. |
| 4,784,130 A | 11/1988 | Kenyon et al. |
| 4,803,981 A | 2/1989 | Vickery |
| 4,807,616 A | 2/1989 | Adahan |
| 4,807,617 A | 2/1989 | Nesti |
| 4,808,160 A | 2/1989 | Timmons et al. |
| 4,813,431 A | 3/1989 | Brown |
| 4,817,897 A | 4/1989 | Kreusel |
| 4,818,320 A | 4/1989 | Weichselbaum |
| 4,823,788 A | 4/1989 | Smith et al. |
| 4,825,859 A | 5/1989 | Lambert |
| 4,827,922 A | 5/1989 | Champain et al. |
| 4,832,014 A | 5/1989 | Perkins |
| 4,838,255 A | 6/1989 | Lambert |
| 4,841,953 A | 6/1989 | Dodrill |
| 4,848,333 A | 7/1989 | Waite |
| 4,850,350 A | 7/1989 | Jackson |
| 4,865,586 A | 9/1989 | Hedberg |
| 4,869,718 A | 9/1989 | Brader |
| 4,899,740 A | 2/1990 | Napolitano |
| 4,905,688 A | 3/1990 | Vicenzi et al. |
| 4,915,103 A | 4/1990 | Visveshwara et al. |
| 4,915,105 A | 4/1990 | Lee |
| 4,919,128 A | 4/1990 | Kopala et al. |
| 4,919,132 A | 4/1990 | Miser |
| 4,938,212 A | 7/1990 | Snook et al. |
| 4,944,310 A | 7/1990 | Sullivan |
| 4,967,743 A | 11/1990 | Lambert |
| 4,971,049 A | 11/1990 | Rotariu et al. |
| 4,982,735 A | 1/1991 | Yagata et al. |

(56) References Cited

U.S. PATENT DOCUMENTS

| | | |
|---|---|---|
| 4,986,269 A | 1/1991 | Hakkinen |
| 4,989,599 A | 2/1991 | Carter |
| 4,990,157 A | 2/1991 | Roberts et al. |
| 5,000,175 A | 3/1991 | Pue |
| 5,002,050 A | 3/1991 | McGinnis |
| 5,005,570 A | 4/1991 | Perkins |
| 5,018,519 A | 5/1991 | Brown |
| 5,022,394 A | 6/1991 | Chmielinski |
| 5,024,219 A | 6/1991 | Dietz |
| 5,025,805 A | 6/1991 | Nutter |
| 5,038,771 A | 8/1991 | Dietz |
| 5,042,478 A | 8/1991 | Kopala et al. |
| 5,046,491 A | 9/1991 | Derrick |
| 5,046,492 A | 9/1991 | Stackhouse et al. |
| 5,048,515 A | 9/1991 | Sanso |
| 5,048,516 A | 9/1991 | Soderberg |
| 5,052,400 A | 10/1991 | Dietz |
| 5,054,484 A | 10/1991 | Hebeler, Jr. |
| 5,058,580 A | 10/1991 | Hazard |
| 5,074,299 A | 12/1991 | Dietz |
| 5,076,267 A | 12/1991 | Pasternack |
| 5,090,408 A | 2/1992 | Spofford et al. |
| 5,097,827 A | 3/1992 | Izumi |
| 5,099,836 A | 3/1992 | Rowland et al. |
| 5,099,837 A | 3/1992 | Russel, Sr. et al. |
| 5,101,820 A | 4/1992 | Christopher |
| 5,103,815 A | 4/1992 | Siegel et al. |
| 5,105,807 A | 4/1992 | Kahn et al. |
| 5,107,830 A | 4/1992 | Younes |
| 5,107,831 A | 4/1992 | Halpern et al. |
| 5,113,857 A | 5/1992 | Dickerman et al. |
| 5,117,818 A | 6/1992 | Palfy |
| 5,117,819 A | 6/1992 | Servidio et al. |
| 5,127,400 A | 7/1992 | DeVries et al. |
| 5,134,995 A | 8/1992 | Gruenke et al. |
| 5,134,996 A | 8/1992 | Bell |
| 5,140,045 A | 8/1992 | Askanazi et al. |
| 5,148,802 A | 9/1992 | Sanders et al. |
| 5,161,525 A | 11/1992 | Kimm et al. |
| 5,165,397 A | 11/1992 | Arp |
| 5,181,509 A | 1/1993 | Spofford et al. |
| 5,184,610 A | 2/1993 | Marten et al. |
| 5,186,167 A | 2/1993 | Kolobow |
| 5,193,532 A | 3/1993 | Moa et al. |
| 5,193,533 A | 3/1993 | Body et al. |
| 5,199,424 A | 4/1993 | Sullivan et al. |
| 5,211,170 A | 5/1993 | Press |
| 5,217,008 A | 6/1993 | Lindholm |
| 5,233,978 A | 8/1993 | Callaway |
| 5,233,979 A | 8/1993 | Strickland |
| 5,239,994 A | 8/1993 | Atkins |
| 5,239,995 A | 8/1993 | Estes et al. |
| 5,243,972 A | 9/1993 | Huang |
| 5,245,995 A | 9/1993 | Sullivan et al. |
| 5,255,675 A | 10/1993 | Kolobow |
| 5,258,027 A | 11/1993 | Berghaus |
| 5,269,296 A | 12/1993 | Landis |
| 5,271,388 A | 12/1993 | Whitwam et al. |
| 5,271,391 A | 12/1993 | Graves |
| 5,275,159 A | 1/1994 | Griebel |
| 5,279,288 A | 1/1994 | Christopher |
| 5,287,852 A | 2/1994 | Arkinstall |
| 5,303,698 A | 4/1994 | Tobia et al. |
| 5,303,700 A | 4/1994 | Weismann et al. |
| 5,318,019 A | 6/1994 | Celaya |
| 5,331,995 A | 7/1994 | Westfall et al. |
| 5,335,656 A | 8/1994 | Bowe et al. |
| 5,339,809 A | 8/1994 | Beck, Jr. et al. |
| 5,349,946 A | 9/1994 | McComb |
| 5,368,017 A | 11/1994 | Sorenson et al. |
| 5,370,112 A | 12/1994 | Perkins |
| 5,373,842 A | 12/1994 | Olsson et al. |
| 5,375,593 A | 12/1994 | Press |
| 5,388,575 A | 2/1995 | Taube |
| 5,394,870 A | 3/1995 | Johansson |
| 5,398,676 A | 3/1995 | Press et al. |
| 5,398,682 A | 3/1995 | Lynn |
| 5,400,778 A | 3/1995 | Jonson et al. |
| 5,419,314 A | 5/1995 | Christopher |
| 5,438,979 A | 8/1995 | Johnson, Jr. et al. |
| 5,438,980 A | 8/1995 | Phillips |
| 5,443,075 A | 8/1995 | Holscher |
| 5,460,174 A | 10/1995 | Chang |
| 5,460,613 A | 10/1995 | Ulrich et al. |
| 5,474,062 A | 12/1995 | DeVires et al. |
| 5,477,852 A | 12/1995 | Landis et al. |
| 5,485,850 A | 1/1996 | Dietz |
| 5,490,502 A | 2/1996 | Rapoport et al. |
| 5,503,146 A | 4/1996 | Froehlich et al. |
| 5,503,497 A | 4/1996 | Dudley et al. |
| 5,507,282 A | 4/1996 | Younes |
| 5,509,409 A | 4/1996 | Weatherholt |
| 5,513,628 A | 5/1996 | Coles et al. |
| 5,513,631 A | 5/1996 | McWilliams |
| 5,513,635 A | 5/1996 | Bedi |
| 5,522,382 A | 6/1996 | Sullivan et al. |
| 5,526,806 A | 6/1996 | Sansoni |
| 5,529,060 A | 6/1996 | Salmon et al. |
| 5,533,506 A | 7/1996 | Wood |
| 5,535,738 A | 7/1996 | Estes et al. |
| 5,537,997 A | 7/1996 | Mechlenburg et al. |
| 5,538,002 A | 7/1996 | Boussignac et al. |
| 5,542,415 A | 8/1996 | Brody |
| 5,546,935 A | 8/1996 | Champeau |
| 5,549,106 A | 8/1996 | Gruenke et al. |
| 5,551,419 A | 9/1996 | Froehlich et al. |
| 5,558,086 A | 9/1996 | Smith et al. |
| 5,564,416 A | 10/1996 | Jones |
| 5,575,282 A | 11/1996 | Knoch et al. |
| 5,582,164 A | 12/1996 | Sanders |
| 5,593,143 A | 1/1997 | Ferrarin |
| 5,595,174 A | 1/1997 | Gwaltney |
| 5,598,837 A | 2/1997 | Sirianne, Jr. et al. |
| 5,598,840 A | 2/1997 | Iund et al. |
| 5,603,315 A | 2/1997 | Sasso, Jr. |
| 5,605,148 A | 2/1997 | Jones |
| 5,626,131 A | 5/1997 | Chua et al. |
| 5,632,269 A | 5/1997 | Zdrojkowski |
| 5,636,630 A | 6/1997 | Miller et al. |
| 5,645,053 A | 7/1997 | Remmers et al. |
| 5,645,054 A | 7/1997 | Cotner et al. |
| 5,647,351 A | 7/1997 | Weismann et al. |
| 5,669,377 A | 9/1997 | Fenn |
| 5,669,380 A | 9/1997 | Garry et al. |
| 5,676,132 A | 10/1997 | Tillotson et al. |
| 5,676,135 A | 10/1997 | McClean |
| 5,682,878 A | 11/1997 | Ogden |
| 5,682,881 A | 11/1997 | Winthrop et al. |
| 5,687,713 A | 11/1997 | Bahr et al. |
| 5,687,714 A | 11/1997 | Kolobow et al. |
| 5,687,715 A | 11/1997 | Landis et al. |
| 5,690,097 A | 11/1997 | Howard et al. |
| 5,692,497 A | 12/1997 | Schnitzer et al. |
| 5,697,364 A | 12/1997 | Chua et al. |
| 5,704,345 A | 1/1998 | Berthon-Jones |
| 5,711,296 A | 1/1998 | Kolobow |
| 5,715,812 A | 2/1998 | Deighan et al. |
| 5,715,815 A | 2/1998 | Lorenzen et al. |
| 5,720,278 A | 2/1998 | Lachmann et al. |
| 5,735,268 A | 4/1998 | Chua et al. |
| 5,735,272 A | 4/1998 | Dillon et al. |
| 5,740,796 A | 4/1998 | Skog |
| 5,752,511 A | 5/1998 | Simmons et al. |
| 5,762,638 A | 6/1998 | Shikani et al. |
| 5,791,337 A | 8/1998 | Coles et al. |
| 5,819,723 A | 10/1998 | Joseph |
| 5,826,579 A | 10/1998 | Remmers et al. |
| 5,845,636 A | 12/1998 | Gruenke et al. |
| 5,865,173 A | 2/1999 | Froehlich |
| 5,865,174 A | 2/1999 | Kloeppel |
| 5,881,723 A | 3/1999 | Wallace et al. |
| 5,904,648 A | 5/1999 | Arndt et al. |
| 5,906,204 A | 5/1999 | Beran et al. |
| 5,911,756 A | 6/1999 | Debry |

(56) References Cited

U.S. PATENT DOCUMENTS

| | | |
|---|---|---|
| 5,915,379 A | 6/1999 | Wallace et al. |
| 5,915,381 A | 6/1999 | Nord |
| 5,918,597 A | 7/1999 | Jones et al. |
| 5,921,238 A | 7/1999 | Bourdon |
| 5,921,942 A | 7/1999 | Remmers et al. |
| 5,921,952 A | 7/1999 | Desmond, III et al. |
| 5,927,276 A | 7/1999 | Rodriguez |
| 5,928,189 A | 7/1999 | Phillips et al. |
| 5,931,160 A | 8/1999 | Gilmore et al. |
| 5,931,162 A | 8/1999 | Christian |
| 5,937,853 A | 8/1999 | Strom |
| 5,937,855 A | 8/1999 | Zdrojkowski et al. |
| 5,938,118 A | 8/1999 | Cooper |
| 5,954,050 A | 9/1999 | Christopher |
| 5,957,136 A | 9/1999 | Magidson et al. |
| 5,964,223 A | 10/1999 | Baran |
| 5,975,077 A | 11/1999 | Hofstetter et al. |
| 5,975,081 A | 11/1999 | Hood et al. |
| 5,979,440 A | 11/1999 | Honkonen et al. |
| 5,989,193 A | 11/1999 | Sullivan |
| 6,000,396 A | 12/1999 | Melker et al. |
| 6,019,101 A | 2/2000 | Cotner et al. |
| 6,039,696 A | 3/2000 | Bell |
| 6,050,260 A | 4/2000 | Daniell et al. |
| 6,076,519 A | 6/2000 | Johnson |
| 6,085,747 A | 7/2000 | Axe et al. |
| 6,091,973 A | 7/2000 | Colla et al. |
| 6,093,169 A | 7/2000 | Cardoso |
| 6,105,575 A | 8/2000 | Estes et al. |
| 6,109,264 A | 8/2000 | Sauer |
| 6,112,746 A | 9/2000 | Kwok et al. |
| 6,119,694 A | 9/2000 | Correa et al. |
| 6,120,460 A | 9/2000 | Abreu |
| 6,123,668 A | 9/2000 | Abreu |
| 6,131,571 A | 10/2000 | Lampotang et al. |
| 6,135,970 A | 10/2000 | Kadhiresan et al. |
| 6,152,132 A | 11/2000 | Psaros |
| 6,152,134 A | 11/2000 | Webber et al. |
| 6,158,432 A | 12/2000 | Biondi et al. |
| 6,192,883 B1 | 2/2001 | Miller, Jr. |
| 6,203,502 B1 | 3/2001 | Hilgendorf et al. |
| 6,213,119 B1 | 4/2001 | Brydon et al. |
| 6,213,955 B1 | 4/2001 | Karakasoglu et al. |
| 6,220,244 B1 | 4/2001 | McLaughlin |
| 6,224,560 B1 | 5/2001 | Gazula et al. |
| 6,227,200 B1 | 5/2001 | Crump et al. |
| 6,247,470 B1 | 6/2001 | Ketchedjian |
| 6,269,811 B1 | 8/2001 | Duff et al. |
| 6,269,812 B1 | 8/2001 | Wallace et al. |
| 6,273,859 B1 | 8/2001 | Remmers et al. |
| 6,286,508 B1 | 9/2001 | Remmers et al. |
| D449,376 S | 10/2001 | McDonald et al. |
| D449,883 S | 10/2001 | McDonald et al. |
| 6,298,850 B1 | 10/2001 | Argraves |
| 6,305,374 B1 | 10/2001 | Zdrojkowski et al. |
| 6,314,957 B1 | 11/2001 | Boissin et al. |
| 6,315,739 B1 | 11/2001 | Merilainen et al. |
| D451,598 S | 12/2001 | McDonald et al. |
| 6,328,038 B1 | 12/2001 | Kessler et al. |
| 6,328,753 B1 | 12/2001 | Zammit |
| 6,332,463 B1 | 12/2001 | Farrugia et al. |
| 6,345,619 B1 | 2/2002 | Finn |
| 6,357,438 B1 | 3/2002 | Hansen |
| 6,357,440 B1 | 3/2002 | Hansen et al. |
| 6,360,741 B2 | 3/2002 | Truschel |
| 6,360,745 B1 | 3/2002 | Wallace et al. |
| 6,363,933 B1 | 4/2002 | Berthon-Jones |
| 6,367,474 B1 | 4/2002 | Berthon-Jones et al. |
| 6,369,838 B1 | 4/2002 | Wallace et al. |
| 6,371,114 B1 | 4/2002 | Schmidt et al. |
| 6,378,520 B1 | 4/2002 | Davenport |
| 6,390,091 B1 | 5/2002 | Banner et al. |
| 6,394,088 B1 | 5/2002 | Frye et al. |
| 6,398,739 B1 | 6/2002 | Sullivan et al. |
| 6,418,928 B1 | 7/2002 | Bordewick et al. |
| 6,422,240 B1 | 7/2002 | Levitsky et al. |
| 6,423,001 B1 | 7/2002 | Abreu |
| 6,427,690 B1 | 8/2002 | McCombs et al. |
| 6,431,172 B1 | 8/2002 | Bordewick |
| 6,439,228 B1 | 8/2002 | Hete et al. |
| 6,439,229 B1 | 8/2002 | Du et al. |
| 6,439,234 B1 | 8/2002 | Curti et al. |
| 6,439,235 B1 | 8/2002 | Larquet et al. |
| 6,450,164 B1 | 9/2002 | Banner et al. |
| 6,450,166 B1 | 9/2002 | McDonald et al. |
| 6,457,472 B1 | 10/2002 | Schwartz et al. |
| 6,467,477 B1 | 10/2002 | Frank et al. |
| 6,478,026 B1 | 11/2002 | Wood |
| 6,494,202 B2 | 12/2002 | Farmer |
| 6,494,206 B1 | 12/2002 | Bergamaschi et al. |
| 6,505,623 B1 | 1/2003 | Hansen |
| 6,505,624 B1 | 1/2003 | Campbell, Sr. |
| 6,516,801 B2 | 2/2003 | Boussignac |
| 6,520,176 B1 | 2/2003 | Dubois et al. |
| 6,520,183 B2 | 2/2003 | Amar |
| 6,530,373 B1 | 3/2003 | Patron et al. |
| 6,532,958 B1 | 3/2003 | Buan et al. |
| 6,532,960 B1 | 3/2003 | Yurko |
| 6,536,432 B2 | 3/2003 | Truschel |
| 6,536,436 B1 | 3/2003 | McGlothen |
| 6,550,478 B2 | 4/2003 | Remmers et al. |
| 6,553,992 B1 | 4/2003 | Berthon-Jones et al. |
| 6,561,188 B1 | 5/2003 | Ellis |
| 6,561,193 B1 | 5/2003 | Noble |
| 6,564,797 B1 | 5/2003 | Mechlenburg et al. |
| 6,564,800 B1 | 5/2003 | Olivares |
| 6,568,391 B1 | 5/2003 | Tatarek et al. |
| 6,571,794 B1 | 6/2003 | Hansen |
| 6,571,796 B2 | 6/2003 | Banner et al. |
| 6,571,798 B1 | 6/2003 | Thornton |
| 6,575,159 B1 | 6/2003 | Frye et al. |
| 6,575,944 B1 | 6/2003 | McNary et al. |
| 6,584,973 B1 | 7/2003 | Biondi et al. |
| 6,588,422 B1 | 7/2003 | Berthon-Jones et al. |
| 6,588,423 B1 | 7/2003 | Sinderby |
| 6,591,834 B1 | 7/2003 | Colla et al. |
| 6,591,835 B1 | 7/2003 | Blanch |
| 6,595,207 B1 | 7/2003 | McDonald et al. |
| 6,595,215 B2 | 7/2003 | Wood |
| 6,609,517 B1 | 8/2003 | Estes et al. |
| 6,622,726 B1 | 9/2003 | Du |
| 6,626,174 B1 | 9/2003 | Genger et al. |
| 6,626,175 B2 | 9/2003 | Jafari et al. |
| 6,629,525 B2 | 10/2003 | Hill et al. |
| 6,629,527 B1 | 10/2003 | Estes et al. |
| 6,629,529 B2 | 10/2003 | Arnott |
| 6,631,919 B1 | 10/2003 | West et al. |
| 6,634,356 B1 | 10/2003 | O'Dea et al. |
| 6,635,021 B1 | 10/2003 | Sullivan et al. |
| 6,640,806 B2 | 11/2003 | Yurko |
| 6,644,305 B2 | 11/2003 | MacRae et al. |
| 6,644,311 B1 | 11/2003 | Truitt et al. |
| 6,644,315 B2 | 11/2003 | Ziaee |
| 6,651,653 B1 | 11/2003 | Honkonen et al. |
| 6,651,656 B2 | 11/2003 | Demers et al. |
| 6,651,658 B1 | 11/2003 | Hill et al. |
| 6,655,382 B1 | 12/2003 | Kolobow |
| 6,655,385 B1 | 12/2003 | Curti et al. |
| 6,666,208 B1 | 12/2003 | Schumacher et al. |
| 6,668,828 B1 | 12/2003 | Figley et al. |
| 6,668,829 B2 | 12/2003 | Biondi et al. |
| 6,669,712 B1 | 12/2003 | Cardoso |
| 6,675,796 B2 | 1/2004 | McDonald |
| 6,675,801 B2 | 1/2004 | Wallace et al. |
| 6,679,265 B2 | 1/2004 | Strickland et al. |
| 6,681,764 B1 | 1/2004 | Honkonen et al. |
| 6,684,883 B1 | 2/2004 | Burns |
| 6,691,702 B2 | 2/2004 | Appel et al. |
| 6,691,707 B1 | 2/2004 | Gunaratnam et al. |
| 6,694,973 B1 | 2/2004 | Dunhao et al. |
| 6,694,978 B1 | 2/2004 | Bennarsten |
| 6,698,423 B1 | 3/2004 | Honkonen et al. |
| 6,705,314 B1 | 3/2004 | O'Dea |
| 6,705,315 B2 | 3/2004 | Sullivan et al. |

(56) References Cited

U.S. PATENT DOCUMENTS

| | | | |
|---|---|---|---|
| 6,722,360 | B2 | 4/2004 | Doshi |
| 6,722,362 | B2 | 4/2004 | Hete et al. |
| 6,742,517 | B1 | 6/2004 | Frye et al. |
| 6,745,768 | B2 | 6/2004 | Colla et al. |
| 6,752,150 | B1 | 6/2004 | Remmers et al. |
| 6,752,151 | B2 | 6/2004 | Hill |
| 6,752,152 | B2 | 6/2004 | Gale et al. |
| 6,755,193 | B2 | 6/2004 | Berthon-Jones et al. |
| 6,758,217 | B1 | 7/2004 | Younes |
| 6,761,172 | B2 | 7/2004 | Boussignac et al. |
| 6,763,832 | B1 | 7/2004 | Kirsch et al. |
| 6,769,432 | B1 | 8/2004 | Keifer |
| 6,776,162 | B2 | 8/2004 | Wood |
| 6,776,163 | B2 | 8/2004 | Dougill et al. |
| 6,789,539 | B2 | 9/2004 | Martinez |
| 6,796,305 | B1 | 9/2004 | Banner et al. |
| 6,799,575 | B1 | 10/2004 | Carter |
| 6,805,126 | B2 | 10/2004 | Dutkiewicz |
| 6,807,966 | B2 | 10/2004 | Wright |
| 6,807,967 | B2 | 10/2004 | Wood |
| 6,810,876 | B2 | 11/2004 | Berthon-Jones |
| 6,814,073 | B2 | 11/2004 | Wickham |
| 6,814,077 | B1 | 11/2004 | Eistert |
| 6,823,866 | B2 | 11/2004 | Jafari et al. |
| 6,827,340 | B2 | 12/2004 | Austin et al. |
| 6,837,238 | B2 | 1/2005 | McDonald |
| 6,840,240 | B1 | 1/2005 | Berthon-Jones et al. |
| 6,843,247 | B2 | 1/2005 | Frye et al. |
| 6,848,446 | B2 | 2/2005 | Noble |
| 6,854,462 | B2 | 2/2005 | Berthon-Jones et al. |
| 6,863,069 | B2 | 3/2005 | Wood |
| 6,866,041 | B2 | 3/2005 | Hardy, Jr. et al. |
| 6,877,511 | B2 | 4/2005 | DeVries et al. |
| 6,880,556 | B2 | 4/2005 | Uchiyama et al. |
| 6,910,480 | B1 | 6/2005 | Berthon-Jones |
| 6,910,482 | B2 | 6/2005 | Bliss et al. |
| 6,910,510 | B2 | 6/2005 | Gale et al. |
| 6,913,601 | B2 | 7/2005 | St. Goar et al. |
| 6,915,803 | B2 | 7/2005 | Berthon-Jones et al. |
| 6,920,875 | B1 | 7/2005 | Hill et al. |
| 6,920,877 | B2 | 7/2005 | Remmers et al. |
| 6,920,878 | B2 | 7/2005 | Sinderby et al. |
| 6,932,084 | B2 | 8/2005 | Estes et al. |
| 6,938,619 | B1 | 9/2005 | Hickle |
| 6,938,620 | B2 | 9/2005 | Payne, Jr. |
| 6,941,950 | B2 | 9/2005 | Wilson et al. |
| 6,948,497 | B2 | 9/2005 | Zdrojkowski et al. |
| 6,951,217 | B2 | 10/2005 | Berthon-Jones |
| 6,971,382 | B1 | 12/2005 | Corso |
| 6,986,353 | B2 | 1/2006 | Wright |
| 6,994,089 | B2 | 2/2006 | Wood |
| 6,997,177 | B2 | 2/2006 | Wood |
| 6,997,881 | B2 | 2/2006 | Green et al. |
| 7,000,612 | B2 | 2/2006 | Jafari et al. |
| 7,004,170 | B1 | 2/2006 | Gillstrom |
| 7,007,692 | B2 | 3/2006 | Aylsworth et al. |
| 7,011,091 | B2 | 3/2006 | Hill et al. |
| 7,013,892 | B2 | 3/2006 | Estes et al. |
| 7,013,898 | B2 | 3/2006 | Rashad et al. |
| 7,017,574 | B2 | 3/2006 | Biondi et al. |
| 7,017,575 | B2 | 3/2006 | Yagi et al. |
| 7,024,945 | B2 | 4/2006 | Wallace |
| 7,036,504 | B2 | 5/2006 | Wallace et al. |
| 7,044,129 | B1 | 5/2006 | Truschel et al. |
| 7,047,969 | B2 | 5/2006 | Noble |
| 7,047,974 | B2 | 5/2006 | Strickland et al. |
| 7,051,735 | B2 | 5/2006 | Mechlenburg et al. |
| 7,055,522 | B2 | 6/2006 | Berthon-Jones |
| 7,059,328 | B2 | 6/2006 | Wood |
| 7,066,173 | B2 | 6/2006 | Banner et al. |
| 7,066,178 | B2 | 6/2006 | Gunaratnam et al. |
| 7,077,132 | B2 | 7/2006 | Berthon-Jones |
| 7,077,133 | B2 | 7/2006 | Yagi et al. |
| 7,080,645 | B2 | 7/2006 | Genger et al. |
| 7,080,646 | B2 | 7/2006 | Wiesmann et al. |
| 7,100,607 | B2 | 9/2006 | Zdrojkowski et al. |
| 7,100,609 | B2 | 9/2006 | Berthon-Jones et al. |
| 7,117,438 | B2 | 10/2006 | Wallace et al. |
| 7,121,277 | B2 | 10/2006 | Strom |
| 7,128,578 | B2 | 10/2006 | Lampotang et al. |
| 7,152,598 | B2 | 12/2006 | Morris et al. |
| 7,152,604 | B2 | 12/2006 | Hickle et al. |
| 7,156,090 | B2 | 1/2007 | Nomori |
| 7,156,097 | B2 | 1/2007 | Cardoso |
| 7,162,296 | B2 | 1/2007 | Leonhardt et al. |
| 7,168,429 | B2 | 1/2007 | Matthews et al. |
| 7,188,621 | B2 | 3/2007 | DeVries et al. |
| 7,188,624 | B2 | 3/2007 | Wood |
| 7,195,016 | B2 | 3/2007 | Loyd et al. |
| 7,195,018 | B1 | 3/2007 | Goldstein |
| 7,201,169 | B2 | 4/2007 | Wilkie et al. |
| 7,201,269 | B2 | 4/2007 | Buscher et al. |
| D542,912 | S | 5/2007 | Gunaratnam et al. |
| 7,222,623 | B2 | 5/2007 | DeVries et al. |
| 7,225,811 | B2 | 6/2007 | Ruiz et al. |
| 7,234,465 | B2 | 6/2007 | Wood |
| 7,237,205 | B2 | 6/2007 | Sarel |
| 7,246,620 | B2 | 7/2007 | Conroy, Jr. |
| D549,323 | S | 8/2007 | Kwok et al. |
| 7,255,103 | B2 | 8/2007 | Bassin |
| 7,255,107 | B1 | 8/2007 | Gomez |
| 7,267,122 | B2 | 9/2007 | Hill |
| 7,267,123 | B2 | 9/2007 | Aylsworth et al. |
| 7,270,126 | B2 | 9/2007 | Wallace et al. |
| 7,270,128 | B2 | 9/2007 | Berthon-Jones et al. |
| 7,296,569 | B2 | 11/2007 | Frye et al. |
| 7,296,573 | B2 | 11/2007 | Estes et al. |
| D557,802 | S | 12/2007 | Miceli, Jr. et al. |
| 7,302,950 | B2 | 12/2007 | Berthon-Jones et al. |
| 7,305,987 | B2 | 12/2007 | Scholler et al. |
| 7,318,437 | B2 | 1/2008 | Gunaratnam et al. |
| 7,320,321 | B2 | 1/2008 | Pranger et al. |
| 7,328,703 | B1 | 2/2008 | Tiep |
| 7,353,826 | B2 | 4/2008 | Sleeper et al. |
| 7,367,337 | B2 | 5/2008 | Berthon-Jones et al. |
| 7,370,652 | B2 | 5/2008 | Matula, Jr. et al. |
| 7,373,939 | B1 | 5/2008 | DuBois et al. |
| 7,406,966 | B2 | 8/2008 | Wondka |
| 7,418,965 | B2 | 9/2008 | Fukunaga et al. |
| 7,422,015 | B2 | 9/2008 | Delisle et al. |
| 7,431,035 | B2 | 10/2008 | Mizuta et al. |
| 7,451,762 | B2 | 11/2008 | Chua et al. |
| 7,455,717 | B2 | 11/2008 | Sprinkle |
| 7,461,656 | B2 | 12/2008 | Gunaratnam et al. |
| 7,468,040 | B2 | 12/2008 | Hartley et al. |
| 7,469,697 | B2 | 12/2008 | Lee et al. |
| 7,472,702 | B2 | 1/2009 | Beck et al. |
| 7,478,641 | B2 | 1/2009 | Rousselet |
| 7,481,219 | B2 | 1/2009 | Lewis et al. |
| 7,481,221 | B2 | 1/2009 | Kullik et al. |
| 7,487,774 | B2 | 2/2009 | Acker |
| 7,487,778 | B2 | 2/2009 | Freitag |
| 7,490,605 | B2 | 2/2009 | Frye et al. |
| D588,258 | S | 3/2009 | Judson et al. |
| D589,139 | S | 3/2009 | Guney et al. |
| 7,500,482 | B2 | 3/2009 | Biederman |
| 7,509,957 | B2 | 3/2009 | Duquette et al. |
| D591,419 | S | 4/2009 | Chandran et al. |
| 7,533,670 | B1 | 5/2009 | Freitag et al. |
| 7,556,038 | B2 | 7/2009 | Kirby et al. |
| 7,559,327 | B2 | 7/2009 | Hernandez |
| 7,562,657 | B2 | 7/2009 | Blanch et al. |
| 7,562,659 | B2 | 7/2009 | Matarasso |
| 7,578,294 | B2 | 8/2009 | Pierro et al. |
| 7,588,033 | B2 | 9/2009 | Wondka |
| 7,591,265 | B2 | 9/2009 | Lee et al. |
| 7,631,642 | B2 | 12/2009 | Freitag et al. |
| 7,640,934 | B2 | 1/2010 | Zollinger et al. |
| 7,658,189 | B2 | 2/2010 | Davidson et al. |
| D614,288 | S | 4/2010 | Judson et al. |
| 7,721,733 | B2 | 5/2010 | Hughes et al. |
| 7,721,736 | B2 | 5/2010 | Urias et al. |
| 7,740,013 | B2 | 6/2010 | Ishizaki et al. |
| 7,743,770 | B2 | 6/2010 | Curti et al. |

(56) References Cited

U.S. PATENT DOCUMENTS

| | | |
|---|---|---|
| 7,762,253 B2 | 7/2010 | Acker et al. |
| 7,766,009 B2 | 8/2010 | Frye et al. |
| 7,787,946 B2 | 8/2010 | Stahmann et al. |
| 7,814,906 B2 | 10/2010 | Moretti |
| 7,819,120 B2 | 10/2010 | Taylor et al. |
| D626,646 S | 11/2010 | Lubke et al. |
| D627,059 S | 11/2010 | Wood et al. |
| 7,832,400 B2 | 11/2010 | Curti et al. |
| 7,837,761 B2 | 11/2010 | Bliss et al. |
| 7,841,343 B2 | 11/2010 | Deane et al. |
| 7,845,350 B1 | 12/2010 | Kayyali et al. |
| 7,849,854 B2 | 12/2010 | DeVries et al. |
| 7,856,982 B2 | 12/2010 | Matula, Jr. et al. |
| 7,866,318 B2 | 1/2011 | Bassin |
| 7,874,290 B2 | 1/2011 | Chalvignac |
| 7,874,291 B2 | 1/2011 | Ging et al. |
| 7,874,293 B2 | 1/2011 | Gunaratnam et al. |
| 7,878,980 B2 | 2/2011 | Ricciardelli |
| 7,882,834 B2 | 2/2011 | Gradon et al. |
| 7,886,740 B2 | 2/2011 | Thomas et al. |
| 7,891,353 B2 | 2/2011 | Chalvignac |
| 7,891,357 B2 | 2/2011 | Carron et al. |
| 7,896,958 B2 | 3/2011 | Sermet et al. |
| 7,900,627 B2 | 3/2011 | Aylsworth et al. |
| 7,900,628 B2 | 3/2011 | Matula, Jr. et al. |
| 7,900,635 B2 | 3/2011 | Gunaratnam et al. |
| 7,901,361 B2 | 3/2011 | Rapoport et al. |
| 7,905,231 B2 | 3/2011 | Chalvignac |
| 7,913,691 B2 | 3/2011 | Farrugia |
| 7,914,459 B2 | 3/2011 | Green et al. |
| 7,918,226 B2 | 4/2011 | Acker et al. |
| 7,926,486 B2 | 4/2011 | Childers |
| 7,926,487 B2 | 4/2011 | Drew et al. |
| 7,931,023 B2 | 4/2011 | Berthon-Jones et al. |
| 7,934,499 B2 | 5/2011 | Berthon-Jones |
| 7,938,114 B2 | 5/2011 | Matthews et al. |
| 7,942,150 B2 | 5/2011 | Guney et al. |
| 7,942,380 B2 | 5/2011 | Bertinetti et al. |
| 7,958,892 B2 | 6/2011 | Kwok et al. |
| 7,975,694 B2 | 7/2011 | Ho |
| 7,980,245 B2 | 7/2011 | Rice et al. |
| 7,987,847 B2 | 8/2011 | Wickham et al. |
| 7,987,850 B2 | 8/2011 | Zollinger et al. |
| 7,987,851 B2 | 8/2011 | Blom et al. |
| 7,992,557 B2 | 8/2011 | Nadjafizadeh et al. |
| 7,997,270 B2 | 8/2011 | Meier |
| 7,997,271 B2 | 8/2011 | Hickle et al. |
| 7,997,272 B2 | 8/2011 | Isaza |
| 8,001,967 B2 | 8/2011 | Wallace et al. |
| D645,557 S | 9/2011 | Scheiner et al. |
| 8,011,365 B2 | 9/2011 | Douglas et al. |
| 8,011,366 B2 | 9/2011 | Knepper |
| 8,015,971 B2 | 9/2011 | Kwok |
| 8,015,974 B2 | 9/2011 | Christopher et al. |
| 8,020,558 B2 | 9/2011 | Christopher et al. |
| 8,025,052 B2 | 9/2011 | Matthews et al. |
| RE42,843 E | 10/2011 | Strickland et al. |
| 8,042,535 B2 | 10/2011 | Kenyon et al. |
| 8,042,537 B2 | 10/2011 | Mechlenburg et al. |
| 8,042,539 B2 | 10/2011 | Chandran et al. |
| 8,042,546 B2 | 10/2011 | Gunaratnam et al. |
| 8,061,354 B2 | 11/2011 | Schneider et al. |
| 8,066,004 B2 | 11/2011 | Morris et al. |
| 2001/0035185 A1 | 11/2001 | Christopher |
| 2001/0035186 A1 | 11/2001 | Hill |
| 2001/0042548 A1 | 11/2001 | Boussignac |
| 2002/0014241 A1 | 2/2002 | Gradon et al. |
| 2002/0017300 A1 | 2/2002 | Hickle et al. |
| 2002/0020930 A1 | 2/2002 | Austin et al. |
| 2002/0026941 A1 | 3/2002 | Biondi et al. |
| 2002/0043264 A1 | 4/2002 | Wickham |
| 2002/0046751 A1 | 4/2002 | MacRae et al. |
| 2002/0046755 A1 | 4/2002 | De Voss |
| 2002/0046756 A1 | 4/2002 | Laizzo et al. |
| 2002/0053346 A1 | 5/2002 | Curti et al. |
| 2002/0055685 A1 | 5/2002 | Levitsky et al. |
| 2002/0059935 A1 | 5/2002 | Wood |
| 2002/0066452 A1 | 6/2002 | Kessler et al. |
| 2002/0078957 A1 | 6/2002 | Remmers et al. |
| 2002/0092527 A1 | 7/2002 | Wood |
| 2002/0112730 A1 | 8/2002 | Dutkiewicz |
| 2002/0153010 A1 | 10/2002 | Rozenberg et al. |
| 2002/0157673 A1 | 10/2002 | Kessler et al. |
| 2002/0159323 A1 | 10/2002 | Makabe et al. |
| 2002/0179090 A1 | 12/2002 | Boussignac |
| 2003/0000522 A1 | 1/2003 | Lynn et al. |
| 2003/0047185 A1 | 3/2003 | Olsen et al. |
| 2003/0069489 A1 | 4/2003 | Abreu |
| 2003/0079749 A1 | 5/2003 | Strickland et al. |
| 2003/0094178 A1 | 5/2003 | McAuley et al. |
| 2003/0111081 A1 | 6/2003 | Gupta |
| 2003/0116163 A1 | 6/2003 | Wood |
| 2003/0121519 A1 | 7/2003 | Estes et al. |
| 2003/0145852 A1 | 8/2003 | Schmidt et al. |
| 2003/0145853 A1 | 8/2003 | Muellner |
| 2003/0145856 A1 | 8/2003 | Zdrojkowski et al. |
| 2003/0150455 A1 | 8/2003 | Bliss et al. |
| 2003/0159696 A1 | 8/2003 | Boussignac et al. |
| 2003/0159697 A1 | 8/2003 | Wallace |
| 2003/0168067 A1 | 9/2003 | Dougill et al. |
| 2003/0213488 A1 | 11/2003 | Remmers et al. |
| 2003/0221687 A1 | 12/2003 | Kaigler |
| 2003/0230308 A1 | 12/2003 | Linden |
| 2004/0020493 A1 | 2/2004 | Wood |
| 2004/0025881 A1 | 2/2004 | Gunaratnam et al. |
| 2004/0035431 A1 | 2/2004 | Wright |
| 2004/0040560 A1 | 3/2004 | Euliano et al. |
| 2004/0050387 A1 | 3/2004 | Younes |
| 2004/0074494 A1 | 4/2004 | Frater |
| 2004/0159323 A1 | 8/2004 | Schmidt et al. |
| 2004/0206352 A1 | 10/2004 | Conroy |
| 2004/0221848 A1 | 11/2004 | Hill |
| 2004/0221854 A1 | 11/2004 | Hete et al. |
| 2004/0226566 A1 | 11/2004 | Gunaratnam et al. |
| 2004/0231674 A1 | 11/2004 | Tanaka |
| 2004/0237963 A1 | 12/2004 | Berthon-Jones |
| 2004/0254501 A1 | 12/2004 | Mault |
| 2004/0255943 A1 | 12/2004 | Morris et al. |
| 2005/0005938 A1 | 1/2005 | Berthon-Jones et al. |
| 2005/0010125 A1 | 1/2005 | Joy et al. |
| 2005/0011524 A1 | 1/2005 | Thomlinson et al. |
| 2005/0016534 A1 | 1/2005 | Ost |
| 2005/0033247 A1 | 2/2005 | Thompson |
| 2005/0034724 A1 | 2/2005 | O'Dea |
| 2005/0061322 A1 | 3/2005 | Freitag |
| 2005/0061326 A1 | 3/2005 | Payne |
| 2005/0072430 A1 | 4/2005 | Djupesland |
| 2005/0081849 A1 | 4/2005 | Warren |
| 2005/0087190 A1 | 4/2005 | Jafari et al. |
| 2005/0098179 A1 | 5/2005 | Burton et al. |
| 2005/0103343 A1 | 5/2005 | Gosweiler |
| 2005/0121033 A1 | 6/2005 | Starr et al. |
| 2005/0121037 A1 | 6/2005 | Wood |
| 2005/0121038 A1 | 6/2005 | Christopher |
| 2005/0150498 A1 | 7/2005 | McDonald |
| 2005/0161049 A1 | 7/2005 | Wright |
| 2005/0166924 A1 | 8/2005 | Thomas et al. |
| 2005/0199242 A1 | 9/2005 | Matula et al. |
| 2005/0205096 A1 | 9/2005 | Matula et al. |
| 2005/0247308 A1 | 11/2005 | Frye et al. |
| 2005/0257793 A1 | 11/2005 | Tatsumoto |
| 2005/0274381 A1 | 12/2005 | Deane et al. |
| 2006/0005834 A1 | 1/2006 | Aylsworth et al. |
| 2006/0005842 A1 | 1/2006 | Rashad et al. |
| 2006/0011199 A1 | 1/2006 | Rashad et al. |
| 2006/0027234 A1 | 2/2006 | Gradon et al. |
| 2006/0048781 A1 | 3/2006 | Nawata |
| 2006/0054169 A1 | 3/2006 | Han et al. |
| 2006/0070625 A1 | 4/2006 | Ayappa et al. |
| 2006/0079799 A1 | 4/2006 | Green et al. |
| 2006/0096596 A1 | 5/2006 | Occhialini et al. |
| 2006/0107958 A1 | 5/2006 | Sleeper |
| 2006/0112959 A1 | 6/2006 | Mechlenburg et al. |
| 2006/0124131 A1 | 6/2006 | Chandran et al. |

(56) References Cited

U.S. PATENT DOCUMENTS

| | | |
|---|---|---|
| 2006/0124134 A1 | 6/2006 | Wood |
| 2006/0137690 A1 | 6/2006 | Gunaratnam et al. |
| 2006/0144396 A1 | 7/2006 | DeVries et al. |
| 2006/0149144 A1 | 7/2006 | Lynn et al. |
| 2006/0150972 A1 | 7/2006 | Mizuta et al. |
| 2006/0150973 A1 | 7/2006 | Chalvignac |
| 2006/0150982 A1 | 7/2006 | Wood |
| 2006/0174877 A1 | 8/2006 | Jagger et al. |
| 2006/0180149 A1 | 8/2006 | Matarasso |
| 2006/0185669 A1 | 8/2006 | Bassovitch |
| 2006/0201504 A1 | 9/2006 | Singhal et al. |
| 2006/0213518 A1 | 9/2006 | DeVries et al. |
| 2006/0213519 A1 | 9/2006 | Schmidt et al. |
| 2006/0225737 A1 | 10/2006 | Iobbi |
| 2006/0237013 A1 | 10/2006 | Kwok |
| 2006/0243278 A1 | 11/2006 | Hamilton et al. |
| 2006/0249155 A1 | 11/2006 | Gambone |
| 2006/0266361 A1 | 11/2006 | Hernandez |
| 2007/0000490 A1 | 1/2007 | DeVries et al. |
| 2007/0000495 A1 | 1/2007 | Matula et al. |
| 2007/0017515 A1 | 1/2007 | Wallace et al. |
| 2007/0056590 A1 | 3/2007 | Wolfson |
| 2007/0062529 A1 | 3/2007 | Choncholas et al. |
| 2007/0068528 A1 | 3/2007 | Bohm et al. |
| 2007/0074724 A1 | 4/2007 | Duquette et al. |
| 2007/0089743 A1 | 4/2007 | Hoffman |
| 2007/0089745 A1 | 4/2007 | Gabriel et al. |
| 2007/0095347 A1 | 5/2007 | Lampotang et al. |
| 2007/0107728 A1 | 5/2007 | Ricciardelli et al. |
| 2007/0107732 A1 | 5/2007 | Dennis et al. |
| 2007/0107737 A1 | 5/2007 | Landis et al. |
| 2007/0113850 A1 | 5/2007 | Acker et al. |
| 2007/0113856 A1 | 5/2007 | Acker et al. |
| 2007/0125379 A1 | 6/2007 | Pierro et al. |
| 2007/0137653 A1 | 6/2007 | Wood |
| 2007/0163600 A1 | 7/2007 | Hoffman |
| 2007/0173705 A1 | 7/2007 | Teller et al. |
| 2007/0181125 A1 | 8/2007 | Mulier |
| 2007/0193705 A1 | 8/2007 | Hsu |
| 2007/0199568 A1 | 8/2007 | Diekens et al. |
| 2007/0209662 A1 | 9/2007 | Bowen et al. |
| 2007/0215156 A1 | 9/2007 | Kwok |
| 2007/0232950 A1 | 10/2007 | West |
| 2007/0240716 A1 | 10/2007 | Marx |
| 2007/0251528 A1 | 11/2007 | Seitz et al. |
| 2007/0272249 A1 | 11/2007 | Chandran et al. |
| 2008/0000475 A1 | 1/2008 | Hill |
| 2008/0006271 A1 | 1/2008 | Aylsworth et al. |
| 2008/0011298 A1 | 1/2008 | Mazar et al. |
| 2008/0011301 A1 | 1/2008 | Qian |
| 2008/0041371 A1 | 2/2008 | Freitag |
| 2008/0041386 A1 | 2/2008 | Dodier et al. |
| 2008/0045815 A1 | 2/2008 | Derchak et al. |
| 2008/0047559 A1 | 2/2008 | Fiori |
| 2008/0051674 A1 | 2/2008 | Davenport et al. |
| 2008/0053438 A1 | 3/2008 | DeVries et al. |
| 2008/0053447 A1 | 3/2008 | Ratajczak et al. |
| 2008/0060646 A1 | 3/2008 | Isaza |
| 2008/0060657 A1 | 3/2008 | McAuley et al. |
| 2008/0066753 A1 | 3/2008 | Martin et al. |
| 2008/0072902 A1 | 3/2008 | Setzer et al. |
| 2008/0078392 A1 | 4/2008 | Pelletier et al. |
| 2008/0078407 A1 | 4/2008 | Sherman |
| 2008/0092904 A1 | 4/2008 | Gunaratnam et al. |
| 2008/0092905 A1 | 4/2008 | Gunaratnam et al. |
| 2008/0092906 A1 | 4/2008 | Gunaratnam et al. |
| 2008/0099024 A1 | 5/2008 | Gunaratnam et al. |
| 2008/0099027 A1 | 5/2008 | Gunaratnam et al. |
| 2008/0105264 A1 | 5/2008 | Gunaratnam et al. |
| 2008/0110462 A1 | 5/2008 | Chekal et al. |
| 2008/0121230 A1 | 5/2008 | Cortez et al. |
| 2008/0135044 A1 | 6/2008 | Freitag et al. |
| 2008/0142019 A1 | 6/2008 | Lewis et al. |
| 2008/0161653 A1 | 7/2008 | Lin et al. |
| 2008/0173304 A1 | 7/2008 | Zaiser et al. |
| 2008/0178880 A1 | 7/2008 | Christopher et al. |
| 2008/0178881 A1 | 7/2008 | Whitcher et al. |
| 2008/0178882 A1 | 7/2008 | Christopher et al. |
| 2008/0185002 A1 | 8/2008 | Berthon-Jones et al. |
| 2008/0185007 A1 | 8/2008 | Sleeper et al. |
| 2008/0190429 A1 | 8/2008 | Tatarek |
| 2008/0190436 A1 | 8/2008 | Jaffe et al. |
| 2008/0196715 A1 | 8/2008 | Yamamori |
| 2008/0196723 A1 | 8/2008 | Tilley |
| 2008/0196728 A1 | 8/2008 | Ho |
| 2008/0202528 A1 | 8/2008 | Carter et al. |
| 2008/0216834 A1 | 9/2008 | Easley et al. |
| 2008/0216838 A1 | 9/2008 | Wondka |
| 2008/0216841 A1 | 9/2008 | Grimes et al. |
| 2008/0223369 A1 | 9/2008 | Warren |
| 2008/0245369 A1 | 10/2008 | Matula et al. |
| 2008/0251079 A1 | 10/2008 | Richey |
| 2008/0264417 A1 | 10/2008 | Manigel et al. |
| 2008/0283060 A1 | 11/2008 | Bassin |
| 2008/0295846 A1 | 12/2008 | Han et al. |
| 2008/0302364 A1 | 12/2008 | Garde et al. |
| 2008/0308104 A1 | 12/2008 | Blomberg et al. |
| 2009/0007911 A1 | 1/2009 | Cleary et al. |
| 2009/0020121 A1 | 1/2009 | Bassin |
| 2009/0044808 A1 | 2/2009 | Guney et al. |
| 2009/0056708 A1 | 3/2009 | Stenzler et al. |
| 2009/0078255 A1 | 3/2009 | Bowman et al. |
| 2009/0078258 A1 | 3/2009 | Bowman et al. |
| 2009/0095298 A1 | 4/2009 | Gunaratnam et al. |
| 2009/0095300 A1 | 4/2009 | McMorrow |
| 2009/0095303 A1 | 4/2009 | Sher et al. |
| 2009/0099471 A1 | 4/2009 | Broadley et al. |
| 2009/0101147 A1 | 4/2009 | Landis et al. |
| 2009/0101154 A1 | 4/2009 | Mutti et al. |
| 2009/0107502 A1 | 4/2009 | Younes |
| 2009/0118632 A1 | 5/2009 | Goepp |
| 2009/0120437 A1 | 5/2009 | Oates et al. |
| 2009/0126739 A1 | 5/2009 | Ng et al. |
| 2009/0133699 A1 | 5/2009 | Nalagatla et al. |
| 2009/0139527 A1 | 6/2009 | Ng et al. |
| 2009/0145435 A1 | 6/2009 | White et al. |
| 2009/0151719 A1 | 6/2009 | Wondka et al. |
| 2009/0151724 A1 | 6/2009 | Wondka et al. |
| 2009/0151726 A1 | 6/2009 | Freitag |
| 2009/0151729 A1 | 6/2009 | Judson et al. |
| 2009/0156953 A1 | 6/2009 | Wondka et al. |
| 2009/0165799 A1 | 7/2009 | Duquette et al. |
| 2009/0173347 A1 | 7/2009 | Berthon-Jones |
| 2009/0173349 A1 | 7/2009 | Hernandez et al. |
| 2009/0183739 A1 | 7/2009 | Wondka |
| 2009/0199855 A1 | 8/2009 | Davenport |
| 2009/0205662 A1 | 8/2009 | Kwok et al. |
| 2009/0241947 A1 | 10/2009 | Bedini et al. |
| 2009/0241951 A1 | 10/2009 | Jafari et al. |
| 2009/0250066 A1 | 10/2009 | Daly |
| 2009/0255533 A1 | 10/2009 | Freitag et al. |
| 2009/0260625 A1 | 10/2009 | Wondka |
| 2009/0277452 A1 | 11/2009 | Lubke et al. |
| 2009/0293877 A1 | 12/2009 | Blanch et al. |
| 2009/0301495 A1 | 12/2009 | Pierro et al. |
| 2009/0308395 A1 | 12/2009 | Lee et al. |
| 2009/0320851 A1 | 12/2009 | Selvarajan et al. |
| 2010/0043786 A1 | 2/2010 | Freitag et al. |
| 2010/0071693 A1 | 3/2010 | Allum et al. |
| 2010/0071697 A1 | 3/2010 | Jafari et al. |
| 2010/0083968 A1 | 4/2010 | Wondka et al. |
| 2010/0108073 A1 | 5/2010 | Zollinger et al. |
| 2010/0132716 A1 | 6/2010 | Selvarajan et al. |
| 2010/0132717 A1 | 6/2010 | Davidson et al. |
| 2010/0163043 A1 | 7/2010 | Hart et al. |
| 2010/0170512 A1 | 7/2010 | Kuypers et al. |
| 2010/0170513 A1 | 7/2010 | Bowditch et al. |
| 2010/0192957 A1 | 8/2010 | Hobson et al. |
| 2010/0218766 A1 | 9/2010 | Milne |
| 2010/0224196 A1 | 9/2010 | Jablons |
| 2010/0252037 A1 | 10/2010 | Wondka et al. |
| 2010/0252039 A1 | 10/2010 | Cipollone et al. |
| 2010/0252040 A1 | 10/2010 | Kapust et al. |
| 2010/0252041 A1 | 10/2010 | Kapust et al. |

(56) References Cited

U.S. PATENT DOCUMENTS

| | | |
|---|---|---|
| 2010/0252042 A1 | 10/2010 | Kapust et al. |
| 2010/0252043 A1 | 10/2010 | Freitag |
| 2010/0252044 A1 | 10/2010 | Duquette et al. |
| 2010/0269834 A1 | 10/2010 | Freitag et al. |
| 2010/0275920 A1 | 11/2010 | Tham et al. |
| 2010/0275921 A1 | 11/2010 | Schindhelm et al. |
| 2010/0282251 A1 | 11/2010 | Calluaud et al. |
| 2010/0282810 A1 | 11/2010 | Hawes |
| 2010/0288279 A1 | 11/2010 | Seiver et al. |
| 2010/0288289 A1 | 11/2010 | Nasir |
| 2010/0300445 A1 | 12/2010 | Chatburn et al. |
| 2010/0300446 A1 | 12/2010 | Nicolazzi et al. |
| 2010/0307487 A1 | 12/2010 | Dunsmore et al. |
| 2010/0307495 A1 | 12/2010 | Kepler et al. |
| 2010/0307499 A1 | 12/2010 | Eger et al. |
| 2010/0307500 A1 | 12/2010 | Armitstead |
| 2010/0307502 A1 | 12/2010 | Rummery et al. |
| 2010/0313891 A1 | 12/2010 | Veliss et al. |
| 2010/0313898 A1 | 12/2010 | Richard et al. |
| 2010/0319703 A1 | 12/2010 | Hayman et al. |
| 2010/0326441 A1 | 12/2010 | Zucker et al. |
| 2010/0326446 A1 | 12/2010 | Behlmaier |
| 2011/0000489 A1 | 1/2011 | Laksov et al. |
| 2011/0009763 A1 | 1/2011 | Levitsky et al. |
| 2011/0011402 A1 | 1/2011 | Berthon-Jones |
| 2011/0023878 A1 | 2/2011 | Thiessen |
| 2011/0023881 A1 | 2/2011 | Thiessen |
| 2011/0034819 A1 | 2/2011 | Desforges et al. |
| 2011/0036352 A1 | 2/2011 | Estes et al. |
| 2011/0041850 A1 | 2/2011 | Vandine et al. |
| 2011/0041855 A1 | 2/2011 | Gunaratnam et al. |
| 2011/0061647 A1 | 3/2011 | Stahmann et al. |
| 2011/0067704 A1 | 3/2011 | Kooij et al. |
| 2011/0067709 A1 | 3/2011 | Doshi et al. |
| 2011/0071444 A1 | 3/2011 | Kassatly et al. |
| 2011/0073107 A1 | 3/2011 | Rodman et al. |
| 2011/0073116 A1 | 3/2011 | Genger et al. |
| 2011/0087123 A9 | 4/2011 | Choncholas et al. |
| 2011/0088690 A1 | 4/2011 | Djupesland et al. |
| 2011/0094518 A1 | 4/2011 | Cipollone et al. |
| 2011/0100365 A1 | 5/2011 | Wedler et al. |
| 2011/0114098 A1 | 5/2011 | McAuley et al. |
| 2011/0125052 A1 | 5/2011 | Davenport et al. |
| 2011/0126841 A1 | 6/2011 | Matula, Jr. et al. |
| 2011/0132363 A1 | 6/2011 | Chalvignac |
| 2011/0139153 A1 | 6/2011 | Chalvignac |
| 2011/0146687 A1 | 6/2011 | Fukushima |
| 2011/0155140 A1 | 6/2011 | Ho et al. |
| 2011/0162650 A1 | 7/2011 | Miller et al. |
| 2011/0162655 A1 | 7/2011 | Gunaratnam et al. |
| 2011/0178419 A1 | 7/2011 | Wood et al. |
| 2011/0180068 A1 | 7/2011 | Kenyon et al. |
| 2011/0197885 A1 | 8/2011 | Wondka et al. |
| 2011/0209705 A1 | 9/2011 | Freitag |
| 2011/0214676 A1 | 9/2011 | Allum et al. |
| 2011/0220105 A1 | 9/2011 | Meier |
| 2011/0232642 A1 | 9/2011 | Bliss et al. |
| 2011/0247625 A1 | 10/2011 | Boussignac |
| 2011/0253147 A1 | 10/2011 | Gusky et al. |
| 2011/0265796 A1 | 11/2011 | Amarasinghe et al. |
| 2011/0277765 A1 | 11/2011 | Christopher et al. |
| 2011/0284003 A1 | 11/2011 | Douglas et al. |

FOREIGN PATENT DOCUMENTS

| | | |
|---|---|---|
| DE | 19841070 | 5/2000 |
| DE | 19849571 | 5/2000 |
| DE | 10337138.9 | 3/2005 |
| DE | 10 2006 023 637.8 | 11/2007 |
| EP | 0125424 | 11/1984 |
| EP | 0692273 | 1/1996 |
| EP | 0778035 | 6/1997 |
| EP | 1359961 | 11/2003 |
| EP | 2377462 | 11/2010 |
| GB | 2174609 | 11/1986 |
| GB | 2201098 | 8/1988 |
| GB | 1055148 | 6/1989 |
| GB | 2338420 | 12/1999 |
| JP | S63-57060 | 3/1998 |
| JP | 2002-204830 | 7/2002 |
| WO | WO-92/11054 | 7/1992 |
| WO | WO-98/01176 | 1/1998 |
| WO | WO-99/04841 | 2/1999 |
| WO | WO-00/64521 | 11/2000 |
| WO | WO-01/76655 | 10/2001 |
| WO | WO-02/062413 | 8/2002 |
| WO | WO-2004/009169 | 1/2004 |
| WO | WO-2005/014091 | 2/2005 |
| WO | WO-2005/018524 | 3/2005 |
| WO | WO-2006/138580 | 12/2006 |
| WO | WO-2007/035804 | 3/2007 |
| WO | WO-2007/139531 | 12/2007 |
| WO | WO-2007142812 | 12/2007 |
| WO | WO-2008/014543 | 2/2008 |
| WO | WO-2008/019102 | 2/2008 |
| WO | WO-2008/052534 | 5/2008 |
| WO | WO-2008/112474 | 9/2008 |
| WO | WO-2008/138040 | 11/2008 |
| WO | WO-2008/144589 | 11/2008 |
| WO | WO-2008/144669 | 11/2008 |
| WO | WO-2009/042973 | 4/2009 |
| WO | WO-2009/042974 | 4/2009 |
| WO | WO-2009/059353 | 5/2009 |
| WO | WO-2009/064202 | 5/2009 |
| WO | WO-2009/074160 | 6/2009 |
| WO | WO-2009/082295 | 7/2009 |
| WO | WO-2009/087607 | 7/2009 |
| WO | WO-2009/092057 | 7/2009 |
| WO | WO-2009/103288 | 8/2009 |
| WO | WO-2009/109005 | 9/2009 |
| WO | WO-2009/115944 | 9/2009 |
| WO | WO-2009/115948 | 9/2009 |
| WO | WO-2009/115949 | 9/2009 |
| WO | WO-2009/129506 | 10/2009 |
| WO | WO-2009/136101 | 11/2009 |
| WO | WO-2009/139647 | 11/2009 |
| WO | WO-2009/149351 | 12/2009 |
| WO | WO-2009/149353 | 12/2009 |
| WO | WO-2009/149355 | 12/2009 |
| WO | WO-2009/149357 | 12/2009 |
| WO | WO-2009/151344 | 12/2009 |
| WO | WO-2009/151791 | 12/2009 |
| WO | WO-2010/000135 | 1/2010 |
| WO | WO-2010/021556 | 2/2010 |
| WO | WO-2010/022363 | 2/2010 |
| WO | WO-2010/039989 | 4/2010 |
| WO | WO-2010/041966 | 4/2010 |
| WO | WO-2010/044034 | 4/2010 |
| WO | WO-2010/057268 | 5/2010 |
| WO | WO-2010/059049 | 5/2010 |
| WO | WO-2010/060422 | 6/2010 |
| WO | WO-2010/068356 | 6/2010 |
| WO | WO-2010/070493 | 6/2010 |
| WO | WO-2010/070497 | 6/2010 |
| WO | WO-2010/070498 | 6/2010 |
| WO | WO-2010/076711 | 7/2010 |
| WO | WO-2010/081223 | 7/2010 |
| WO | WO-2010/091157 | 8/2010 |
| WO | WO-2010/099375 | 9/2010 |
| WO | WO-2010/102094 | 9/2010 |
| WO | WO-2010/115166 | 10/2010 |
| WO | WO-2010/115168 | 10/2010 |
| WO | WO-2010/115169 | 10/2010 |
| WO | WO-2010/115170 | 10/2010 |
| WO | WO-2010/116275 | 10/2010 |
| WO | WO-2010/132853 | 11/2010 |
| WO | WO-2010/136923 | 12/2010 |
| WO | WO-2010/139014 | 12/2010 |
| WO | WO-2010/150187 | 12/2010 |
| WO | WO-2011/002608 | 1/2011 |
| WO | WO-2011/004274 | 1/2011 |
| WO | WO-2011/006184 | 1/2011 |
| WO | WO-2011/006199 | 1/2011 |

(56) References Cited

FOREIGN PATENT DOCUMENTS

| WO | WO-2011/014931 | 2/2011 |
|---|---|---|
| WO | WO-2011/017033 | 2/2011 |
| WO | WO-2011/017738 | 2/2011 |
| WO | WO-2011/021978 | 2/2011 |
| WO | WO-2011/022779 | 3/2011 |
| WO | WO-2011/024383 | 3/2011 |
| WO | WO-2011/029073 | 3/2011 |
| WO | WO-2011/029074 | 3/2011 |
| WO | WO-2011/035373 | 3/2011 |
| WO | WO-2011/038950 | 4/2011 |
| WO | WO-2011/038951 | 4/2011 |
| WO | WO-2011/044627 | 4/2011 |
| WO | WO-2011/057362 | 5/2011 |
| WO | WO 2011/059346 | 5/2011 |
| WO | WO-2011/061648 | 5/2011 |
| WO | WO-2011/062510 | 5/2011 |
| WO | WO-2011/086437 | 7/2011 |
| WO | WO-2011/086438 | 7/2011 |
| WO | WO-2011/112807 | 9/2011 |

OTHER PUBLICATIONS

In the U.S. Patent and Trademark Office, Supplemental Notice of Allowance dated in re: U.S. Appl. No. 10/771,803, dated Nov. 7, 2008, 2 pages.
In the U.S. Patent and Trademark Office, Examiners Interview Summary in re: U.S. Appl. No. 10/771,803, dated Oct. 31, 2008, 4 pages.
In the U.S. Patent and Trademark Office, Notice of Allowance dated in re: U.S. Appl. No. 10/771,803, dated Oct. 20, 2008, 8 pages.
In the U.S. Patent and Trademark Office, Examiners Interview Summary in re: U.S. Appl. No. 10/771,803, dated Nov. 2, 2007, 2 pages.
In the U.S. Patent and Trademark Office, Office Action in re: U.S. Appl. No. 10/771,803, dated Jun. 14, 2007, 12 pages.
In the U.S. Patent and Trademark Office, Restriction Requirement in re: U.S. Appl. No. 12/271,484, dated Feb. 9, 2011, 5 pages.
In the U.S. Patent and Trademark Office, Restriction Requirement in re: U.S. Appl. No. 12/754,437, dated Aug. 16, 2011, 5 pages.
In the U.S. Patent and Trademark Office, Non-Final Office Action dated in re: U.S. Appl. No. 10/567,746, dated Oct. 5, 2009, 9 pages.
In the U.S. Patent and Trademark Office, Notice of Allowance and Examiners Interview Summary in re: U.S. Appl. No. 11/523,519, dated Jan. 16, 2009, 10 pages.
In the U.S. Patent and Trademark Office, Examiners Interview Summary in re: U.S. Appl. No. 11/523,519, dated Jan. 13, 2009, 4 pages.
In the U.S. Patent and Trademark Office, Final Office Action in re: U.S. Appl. No. 11/523,519, dated Jul. 11, 2008, 13 pages.
In the U.S. Patent and Trademark Office, Examiners Interview Summary in re: U.S. Appl. No. 11/523,519, dated Apr. 10, 2008, 3 pages.
In the U.S. Patent and Trademark Office, Final Office Action in re: U.S. Appl. No. 11/523,519, dated Nov. 26, 2007, 14 pages.
In the U.S. Patent and Trademark Office, Office Action in re: U.S. Appl. No. 11/523,519, dated Mar. 7, 2007, 11 pages.
In the U.S. Patent and Trademark Office, Restriction Requirement in re: U.S. Appl. No. 11/523,518, dated Dec. 30, 2009, 4 pages.
In the U.S. Patent and Trademark Office, Supplemental Notice of Allowance in re: U.S. Appl. No. 11/798,965, dated Aug. 21, 2009, 4 pages.
In the U.S. Patent and Trademark Office, Notice of Allowance in re: U.S. Appl. No. 11/798,965, dated Jul. 17, 2009, 5 pages.
In the U.S. Patent and Trademark Office, Final Office Action in re: U.S. Appl. No. 11/798,965, dated Apr. 9, 2009, 6 pages.
In the U.S. Patent and Trademark Office, Office Action in re: U.S. Appl. No. 11/798,965, dated Jul. 29, 2008, 12 pages.
In the U.S. Patent and Trademark Office, Office Action in re: U.S. Appl. No. 12/578,283, dated Oct. 19, 2011, 5 pages.
In the U.S. Patent and Trademark Office, Restriction/Election Requirement in re: U.S. Appl. No. 11/882,530, dated Apr. 27, 2011, 5 pages.
In the U.S. Patent and Trademark Office, Supplemental Notice of Allowance in re: U.S. Appl. No. 10/870,849, dated Jun. 16, 2009, 2 pages.
In the U.S. Patent and Trademark Office, Notice of Allowance in re: U.S. Appl. No. 10/870,849, dated Jun. 3, 2009, 4 pages.
In the U.S. Patent and Trademark Office, Notice of Allowance in re: U.S. Appl. No. 10/870,849, dated May 14, 2009, 8 pages.
In the U.S. Patent and Trademark Office, Restriction in re: U.S. Appl. No. 10/870,849, dated Nov. 16, 2007, 5 pages.
In the U.S. Patent and Trademark Office, Examiners Interview Summary in re: U.S. Appl. No. 10/870,849, dated Jul. 27, 2007, 2 pages.
In the U.S. Patent and Trademark Office, Office Action in re: U.S. Appl. No. 10/870,849, dated Feb. 22, 2007, 13 pages.
In the U.S. Patent and Trademark Office, Restriction/Election Requirement in re: U.S. Appl. No. 12/493,677, dated Aug. 5, 2011, 5 pages.
In the U.S. Patent and Trademark Office, Restriction/Election Requirement in re: U.S. Appl. No. 12/153,423, dated Oct. 6, 2011, 8 pages.
In the U.S. Patent and Trademark Office, Notice of Allowance in re: U.S. Appl. No. 10/922,054, dated Feb. 12, 2008, 6 pages.
In the U.S. Patent and Trademark Office, Final Office Action in re: U.S. Appl. No. 10/922,054, dated Nov. 27, 2007, 9 pages.
In the U.S. Patent and Trademark Office, Office Action in re: U.S. Appl. No. 10/922,054, dated Mar. 14, 2007, 14 pages.
In the U.S. Patent and Trademark Office, Office Action in re: U.S. Appl. No. 10/922,054, dated Sep. 7, 2006, 21 pages.
In the U.S. Patent and Trademark Office, Restriction Requirement in re: U.S. Appl. No. 10/922,054, dated May 17, 2006, 5 pages.
In the U.S. Patent and Trademark Office, Notice of Allowance and Examiners Interview Summary in re: U.S. Appl. No. 12/076,062, dated Nov. 2, 2011, 8 pages.
In the U.S. Patent and Trademark Office, Office Action in re: U.S. Appl. No. 12/076,062, dated Jan. 13, 2011, 14 pages.
In the U.S. Patent and Trademark Office, Office Action in re: U.S. Appl. No. 12/355,753, dated Sep. 28, 2011, 32 pages.
In the U.S. Patent and Trademark Office, *Ex Parte Quayle* Office Action in re: U.S. Appl. No. 29/388,700, dated Oct. 7, 2011, 5 pages.
"AARC Clinical Practice Guideline: Oxygen Therapy in the Home or Extended Care Facility," *Resp. Care*, 1992: 37(8), pp. 918-922.
"ATS Statement: Guidelines for the Six-Minute Walk Test," *Am. J. Respir. Crit. Care Med.*, 2002: 166, pp. 111-117.
"Passy-Muir Speaking Valves," *Respiratory*, Nov. 13, 1998, 7 pages.
Ambrosino, "Exercise and noninvasive ventilatory support," *Monaldi Arch Chest Dis.*, 2000: 55(3): 242-246.
Ambrosino, "Weaning and Respiratory Muscle Dysfunction: The Egg Chicken Dilemma," *Chest*, 2005: 128(2), pp. 481-483.
Bach et al., "Intermittent Positive Pressure Ventilation via Nasal Access in the Management of Respiratory Insufficiency," *Chest*, 1987: 92(1), pp. 168-170.
Banner et al., "Extubating at a Pressure Support Ventilation Level Corresponding to Zero Imposed Work of Breathing," *Anesthesiology*, Sep. 1994: 81(3A), p. A271.
Banner et al., "Imposed Work of Breathing and Methods of Triggering a Demand-Flow, Continuous Positive Airway Pressure System," *Critical Care Medicine*, 1993: 21(2), pp. 183-190.
Banner et al., "Site of Pressure Measurement During Spontaneous Breathing with Continuous Positive Airway Pressure: Effect on Calculating Imposed Work of Breathing," *Critical Care Medicine*, 1992: 20(4), pp. 528-533.
Barakat et al., "Effect of noninvasive ventilatory support during exercise of a program in pulmonary rehabilitation in patients with COPD," *Int. J. Chron. Obstruct. Pulmon. Dis.*, 2007: 2(4), pp. 585-591.
Barreiro et al., "Noninvasive ventilation," Crit Care Clin., 2007; 23(2): 201-22.
Bauer et al., "ADAM Nasal CPAP Circuit Adaptation: a Case Report," *Sleep*, 1991: 14(3), pp. 272-273.
Blanch, "Clinical Studies of Tracheal Gas Insufflation," *Resp. Care*, 2001: 45(2), pp. 158-166.
Borghi-Silva et al., "Non-invasive ventilation improves peripheral oxygen saturation and reduces fatigability of quadriceps in patients with COPD," Respirology, 2009, 14:537-546.
Bossi et al., "Continuous Positive Airway Pressure in the Spontaneously Breathing Newborn by Means of Bilateral Nasal Cannulation," *Monatsschr Kinderheilkd*, 1975: 123(4), pp. 141-146.

(56) References Cited

OTHER PUBLICATIONS

Boussarsar et al., "Relationship between ventilatory settings and barotrauma in the acute respiratory distress syndrome," *Intensive Care Med.*, 2002: 28(4): 406-13.

Chang et al., "Reduced Inspiratory Muscle Endurance Following Successful Weaning From Prolonged Mechanical Ventilation," *Chest*, 2005: 128(2), pp. 553-559.

Charlotte Regional Medical Center, "Application of the Passy-Muir Tracheostomy and Ventilator," *Speech-Language Pathology Department*, Jan. 1995, 8 pages.

Christopher et al., "Preliminary Observations of Transtracheal Augmented Ventilation for Chronic Severe Respiratory Disease," *Resp. Care*, 2001: 46(1), pp. 15-25.

Christopher, et al., "Transtracheal Oxygen Therapy for Refractory Hypoxemia," *JAMA*, 1986: 256(4), pp. 494-497.

Ciccolella et al.; "Administration of High-Flow, Vapor-phased, Humidified Nasal Cannula Air (HF-HNC) Decreases Work of Breathing (WOB) in Healthy Subjects During Exercise," *AmJRCCM*, Apr. 2001: 163(5), Part 2, pp. A622. (Abstract Only).

Clini et al., "The Italian multicentre study on noninvasive ventilation in chronic obstructive pulmonary disease patients," *Eur. Respir. J.*, 2002, 20(3): 529-538.

Costa et al., "Influence of noninvasive ventilation by BiPAP® on exercise tolerance and respiratory muscle strength in chronic obstructive pulmonary disease patients (COPD)," *Rev. Lat. Am. Enfermagem.*, 2006: 14(3), pp. 378-382.

Diaz et al., "Breathing Pattern and Gas Exchange at Peak Exercise in COPD Patients With and Without Tidal Flow Limitation at Rest," *European Respiratory Journal*, 2001: 17, pp. 1120-1127.

Enright, "The six-minute walk test," *Resp. Care*, 2003: 8, pp. 783-785.

Ferreira et al., "Trigger Performance of Mid-level ICU Mechanical Ventilators During Assisted Ventilation: A Bench Study," *Intensive Care Medicine*, 2008,34:1669-1675.

Fink, "Helium-Oxygen: An Old Therapy Creates New Interest," *J. Resp. Care. Pract. now RT for Decision Makers in Respiratory Care*, 1999, pp. 71-76.

Gaughan et al., "A Comparison in a Lung Model of Low- and High-Flow Regulators for Transtracheal Jet Ventilation," *Anesthesiology*, 1992: 77(1), pp. 189-199.

Gregoretti, et al., "Transtracheal Open Ventilation in Acute Respiratory Failure Secondary to Severe Chronic Obstructive Pulmonary Disease Exacerbation," *Am. J. Resp. Crit. Care. Med.*, 2006: 173(8), pp. 877-881.

Haenel et al., "Efficacy of Selective Intrabronchial Air Insufflation in Acute Lobar Colapse," *Am. J. Surg.*, 1992: 164(5), pp. 501-505.

Keilty et al., "Effect of inspiratory pressure support on exercise tolerance and breathlessness in patients with severe stable chronic obstructive pulmonary disease," *Thorax*, 1994, 49(10): 990-994.

Köhnlein et al., "Noninvasive ventilation in pulmonary rehabilitation of COPD patients," *Respir. Med.*, 2009, 103: 1329-1336.

Koska et al., "Evaluation of a Fiberoptic System for Airway Pressure Monitoring," *J. Clin. Monit.*, 1993: 10(4), pp. 247-250.

Lewis, "Breathless No More, Defeating Adult Sleep Apnea," *FDA Consumer Magazine*, Jun. 1992, pp. 33-37.

Limberg et al., "Changes in Supplemental Oxygen Prescription in Pulmonary Rehabilitation," *Resp. Care*, 2006:51(11), p. 1302.

Macinryre, "Long-Term Oxygen Therapy: Conference Summary," *Resp. Care*, 2000: 45(2), pp. 237-245.

Macintyre et al., "Acute exacerbations and repiratory failure in chronic obstructive pulmonary disease," *Proc. Am. Thorac. Soc.*, 2008: 5(4), pp. 530-535.

Massie et al., "Clinical Outcomes Related to Interface Type in Patients With Obstructive Sleep Apnea/Hypopnea Syndrome Who Are Using Continuous Positive Airway Pressure," *Chest*, 2003: 123(4), pp. 1112-1118.

McCoy, "Oxygen Conservation Techniques and Devices," *Resp. Care*, 2000: 45(1), pp. 95-104.

McGinley, "A nasal cannula can be used to treat obstructive sleep apnea"; *Am. J. Resp. Crit. Care Med.*, 2007: 176(2), pp. 194-200.

Menadue et al., "Non-invasive ventilation during arm exercise and ground walking in patients with chronic hypercapnic respiratory failure," *Respirology*, 2009, 14(2): 251-259.

Menon et al., "Tracheal Perforation. A Complication Associated with Transtracheal Oxygen Therapy," *Chest*, 1993: 104(2), pp. 636-637.

Messinger et al., "Tracheal Pressure Triggering a Demand-Flow CPAP System Decreases Work of Breathing," *Anesthesiology*, 1994: 81(3A), p. A272.

Messinger et al., "Using Tracheal Pressure to Trigger the Ventilator and Control Airway Pressure During Continuous Positive Airway Pressure Decreases Work of Breathing," *Chest*, 1995: vol. 108(2), pp. 509-514.

Mettey, "Use of CPAP Nasal Cannula for Aids of the Newborns in Tropical Countries," *Medecine Tropicale*, 1985: 45(1), pp. 87-90.

Nahmias et al., "Treatment of the Obstructive Sleep Apnea Syndrome Using a Nasopharyngeal Tube", *Chest*, 1988:94(6), pp. 1142-1147.

Nava et al., "Non-invasive ventilation," *Minerva Anestesiol.*, 2009: 75(1-2), pp. 31-36.

Passy-Muir Inc., "Clinical Inservice Outline", Apr. 2004, 19 pages.

Peters et al., "Combined Physiological Effects of Bronchodilators and Hyperoxia on Exertional Dyspnea in Normoxic COPD," *Thorax*, 2006: 61, pp. 559-567.

Polkey et al., "Inspiratory pressure support reduces slowing of inspiratory muscle relations rate during exhaustive treadmill walking in sever COPD," *Am. J. Resp. Crit. Care Med.*, 1996: 154(4, 10), pp. 1146-1150.

Porta et al., "Mask proportional assist vs pressure support ventilation in patients in clinically stable condition with chronic venilatory failure," *Chest*, 2002: 122(2), pp. 479-488.

Prigent et al., "Comparative Effects of Two Ventilatory Modes on Speech in Tracheostomized Patients with Neuromuscular Disease," *Am. J. Resp. Crit. Care Med.*, 2003: 167(8), pp. 114-119.

Puente-Maestu et al., "Dyspnea, Ventilatory Pattern, and Changes in Dynamic Hyperinflation Related to the Intensity of Constant Work Rate Exercise in COPD," *Chest*, 2005: 128(2), pp. 651-656.

Ram et al., "Non-invasive positive pressure ventilation for treatment of respiratory failure due to exacerbations of chroic obstructive pulmonary disease," *Cochrane Database Syst Rev.*, 2004(3):1-72.

Rothe et al., "Near Fatal Complication of Transtracheal Oxygen Therapy with the Scoop(R) System," *Pneumologie*, 1996: 50(10), pp. 700-702. (English Abstract provided.).

Rothfleisch et al., "Facilitation of fiberoptic nasotracheal intubation in a morbidly obese patient by simultaneous use of nasal CPAP," *Chest*, 1994, 106(1): 287-288.

Sanders et al., "CPAP Via Nasal Mask: A Treatment for Occlusive Sleep Apnea," *Chest*, 1983: 83(1), pp. 144-145.

Sinderby et al., "Neural control of mechanical ventilation in respiratory failure," *Nat. Med.*, 1999: 5(12), pp. 1433-1436.

Somfay et al., "Dose-Response Effect of Oxygen on Hyperinflation and Exercise Endurance in Nonhypoxaemic COPD Patients," *Eur. Resp. J.*, 2001: 18, pp. 77-84.

Sullivan et al., "Reversal of Obstructive Sleep Apnoea by Continuous Positive Airway Pressure Applied Through the Nares," *The Lancet*, 1981: 1(8225), pp. 862-865.

Sullivan, "Home treatment of obstructive sleep apnoea with continuous positive airway pressure applied through a nose-mask," *Bull Eur Physiopathol Respir.*, 1984: 20(1), pp. 49-54.

Tiep et al., "Pulsed nasal and transtracheal oxygen delivery," *Chest*, 1990: 97, pp. 364-368.

Tsuboi et al., "Ventilatory Support During Exercise in Patients With Pulmonary Tuberculosis Sequelae," *Chest*, 1997: 112(4), pp. 1000-1007.

*VHA/DOD Clinical Practice Guideline*, "Management of Chronic Obstructive Pulmonary Disease," Aug. 1999, Ver. 1.1a, Updated Nov. 1999.

Wijkstra et al., "Nocturnal non-invasive positive pressure ventilation for stable chronic obstructive pulmonary disease," *Cochrane Database Syst. Rev.*, 2002, 3: 1-22.

Yaeger et al., "Oxygen Therapy Using Pulse and Continuous Flow With a Transtracheal Catheter and a Nasal Cannula," *Chest*, 1994: 106, pp. 854-860.

(56) References Cited

OTHER PUBLICATIONS

Walsh, "McGraw Hill Pocket reference Machinists' and Metalworker Pocket Reference," *New York McGraw-Hill*, 2000, pp. 3-67, submitting 3 pages.
International Preliminary Report and Written Opinion on Patentability for PCT/DE2004/001646, dated Jul. 3, 2006.
European patent Office Search Report issued Oct. 19, 2007 in co-pending EP 04762494.
International Search Report and Written Opinion for PCT/US04/26800 issued Jun. 22, 2006.
International Search Report and Written Opinion for PCT/US07/12108, dated Aug. 8, 2008.
International Search Report and Written Opinion for PCT/US07/17400, dated Apr. 28, 2008.
International Search Report and Written Opinion for PCT/US08/64015, dated Sep. 26, 2008.
International Search Report and Written Opinion for PCT/US08/64164, dated Sep. 29, 2008.
International Search Report and Written Opinion for PCT/US08/78031, dated Nov. 24, 2008.
International Search Report and Written Opinion for PCT/US08/78033, dated Dec. 3, 2008.
International Search Report and Written Opinion for PCT/US09/054673, dated Oct. 8, 2009.
International Search Report and Written Opinion for PCT/US09/41027, dated Dec. 14, 2009.
International Search Report and Written Opinion for PCT/US09/59272, dated Dec. 2, 2009.
International Search Report and Written Opinion for PCT/US2006/036600, dated Apr. 3, 2007.
International Search Report and Written Opinion for PCT/US2009/031355 issued Mar. 11, 2009.
International Search Report and Written Opinion for PCT/US2009/041034, dated Jun. 10, 2009.
International Search Report and Written Opinion for PCT/US2010/029871, dated Jul. 12, 2010.
International Search Report and Written Opinion for PCT/US2010/029873, dated Jun. 28, 2010.
International Search Report and Written Opinion for PCT/US2010/029874, dated Jul. 12, 2010.
International Search Report and Written Opinion for PCT/US2010/029875, dated Jul. 12, 2010.
International Search Report and Written Opinion for PCT/US2010/047920, dated Nov. 1, 2010.
International Search Report and Written Opinion for PCT/US2010/047921, dated Jan. 27, 2011.
International Search Report for PCT/DE2004/001646, dated Jan. 17, 2005.

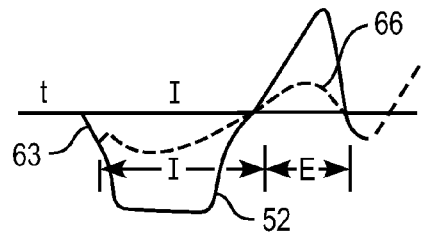
FIG. 4A
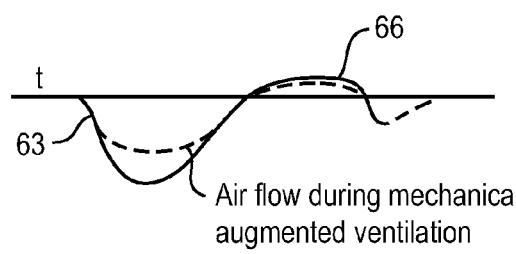
FIG. 4B
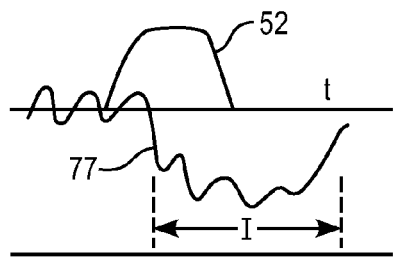
FIG. 4C
FIG. 5
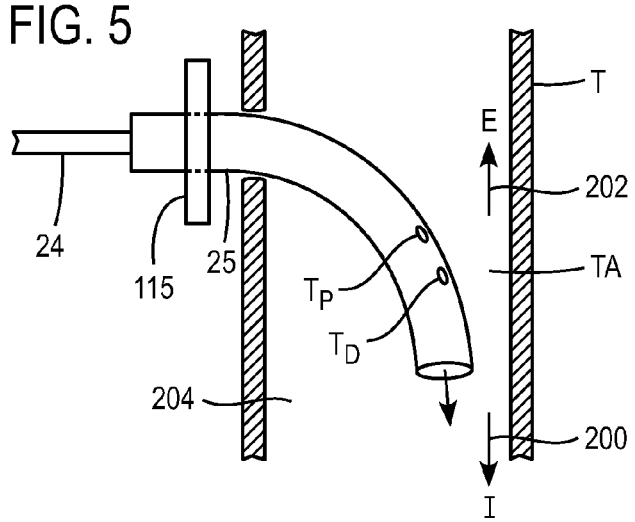
FIG. 5A
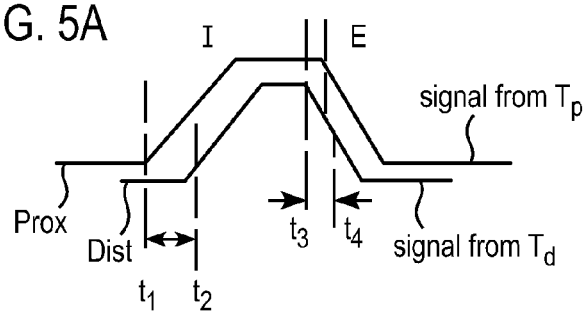

$$\frac{b/a}{CSA} \cdot X = \text{Flow Rate}$$

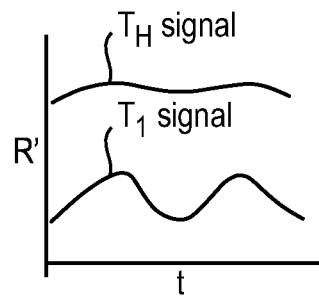
FIG. 8B
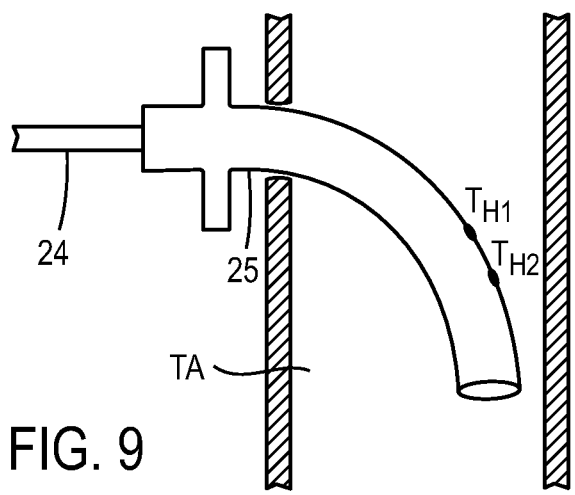
FIG. 9
FIG. 9A
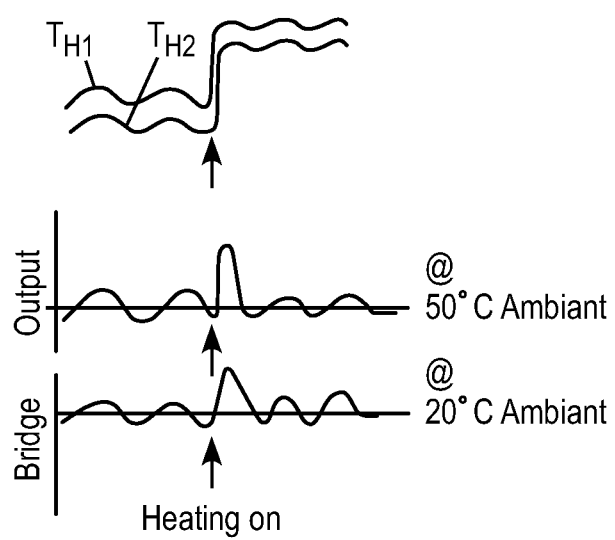
FIG. 9B

50° C Ambiant

20° C Ambiant

FIG. 11A
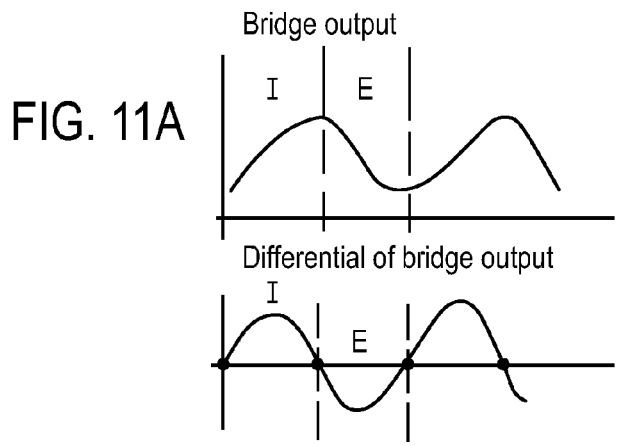
FIG. 12
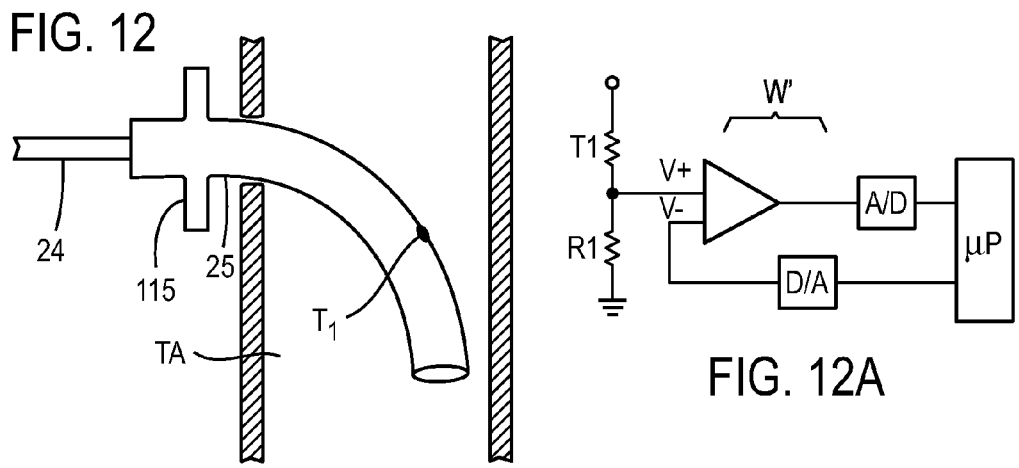
FIG. 12A
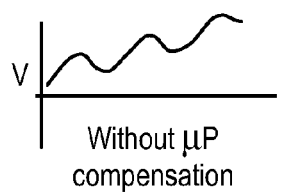
FIG. 12B
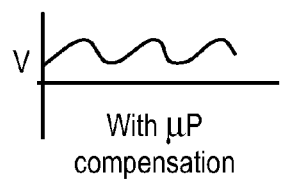
FIG. 12C
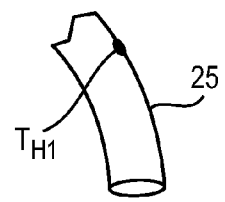
FIG. 12D
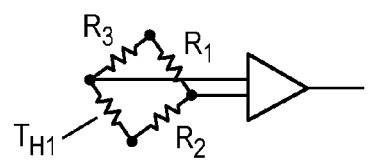
FIG. 12E $$C = \frac{\int Q}{P}; \quad R = \frac{P \cdot t}{\int Q}; \quad WOB' = \frac{1}{L}$$

DETAIL E

SECTION C-C

SECTION D-D

METHODS AND DEVICES FOR SENSING RESPIRATION AND CONTROLLING VENTILATOR FUNCTIONS

CROSS-REFERENCE TO RELATED APPLICATIONS

This application claims priority to U.S. Provisional Patent Application No. 61/071,251, entitled "Methods and Devices for Sensing Respiration and Controlling Ventilator Functions", filed Apr. 18, 2008, the content of which is incorporated by reference in its entirety.

This application incorporates by reference in their entireties: U.S. patent application Ser. No. 10/771,803, entitled "Method and Arrangement for Respiratory Support for a Patient Airway Prosthesis and Catheter", filed Feb. 4, 2004; U.S. patent application Ser. No. 11/523,518, entitled "Systems, Methods and Apparatus for Respiratory Support of a Patient", filed Sep. 20, 2006; and U.S. patent application Ser. No. 11/523,519, entitled "Systems, Methods and Apparatus for Respiratory Support of a Patient", filed Sep. 20, 2006.

FIELD OF THE INVENTION

This invention relates to ventilation therapy for persons requiring respiratory support from a ventilator. Conditions can include respiratory impairment and breathing disorders, such as chronic obstructive pulmonary disease (COPD), pulmonary fibrosis, acute respiratory distress syndrome (ARDS), neuromuscular impairment, and sleep apnea, or anesthesia, emergency and the like. The present invention relates more specifically to measuring a patient's respiratory pattern using breath sensing approaches, and using that measured information from breath sensors to synchronize ventilator output to a breathing pattern of a patient.

BACKGROUND OF THE INVENTION

There are two general types of control systems for conventional ventilators. A first type delivers gas to a patient based on a frequency selected by the clinician that is independent of patient activity. This control system is used when the patient is non-alert, sedated, unresponsive or paralyzed. In this type of system, the ventilator is breathing for the patient. A second type of control system delivers gas to the patient in response to an inspiratory effort created by the patient. This type of ventilation helps the patient breathe. There are also ventilators and modes of ventilation that combine these two types of control systems. The present invention relates to ventilation systems and modes that respond to an inspiratory effort by the patient.

Control systems that respond to patient breathing efforts require breath sensors to detect inspiration. Conventional systems use pressure or flow sensors to detect the start of an inspiratory effort by the patient. The sensor is located somewhere in-line with the ventilation gas delivery circuit, either inside the ventilator, or in the tubing between the ventilator and the patient, or at the patient end of the tubing. In-line breath sensors are also used to measure the entire respiratory curve in addition to just the start of inspiration, however because the gas being delivered by the ventilator also moves past the sensor, the sensor during that time no longer measures the patient's respiration but rather the ventilator activity. In a closed ventilation system, the patient lung pressure and the gas delivery circuit pressure, while not necessarily identical, are typically very close. In an open ventilation system in which the patient is also spontaneously breathing, the patient lung pressure and the gas delivery circuit pressure can be very different. In this case a breath sensor in-line with the ventilation gas delivery circuit can be ineffective in measuring the entire respiratory pattern.

In ventilation systems in which the patient is expected to be breathing or partially breathing spontaneously, synchronization between the ventilator and the patient is important for comfort and efficacy. However, poor synchrony is still reported in some cases because of the demanding and exacting task of measuring all the different possible spontaneous breathing signals and the vast range of variations that exist.

Some attempts have been made to use sensors that are in parallel with the ventilation gas delivery system and are more directly coupled to the patient's actual respiration. The intent of these systems is to improve breath detection, to improve responsiveness of the ventilator, to improve the synchrony of the ventilator to the patient, or to reduce work of breathing required for a patient to trigger the ventilator.

For example, chest impedance sensors can be used to measure the entire respiratory curve of a patient and to use that signal to control the ventilator and synchronize the ventilator to the patient's breathing. However, this approach is technically challenging because the signal is prone to drift, noise and artifacts caused by patient motion and abdominal movement. In another technology, the neural respiratory drive measured with an esophageal catheter is used to measure the respiration of a patient. However, this technique requires an additional invasive device, and it does not monitor exhalation activity since that is a neurally passive function.

Thermal breath sensing is promising because it can be implemented such that the breath sensing can be placed in parallel with ventilation gas delivery and in-line with the spontaneous breathing airflow. If implemented correctly, thermal sensors can determine the complete breathing pattern of the patient and can generate a signal that is not disrupted by the ventilator gas flow. This is advantageous to optimize the synchrony of the ventilator to the patient's natural breath pattern, so that the patient is comfortable. Also, if the goal is to provide therapy during different portions of the respiratory curve, such as during the middle of inspiration, or during a particular part of the expiratory phase, then this method which accurately measures the entire respiratory curve is very beneficial. Another advantage of thermal sensing is that it is possible to correlate the signal to the patient's spontaneous breathing airflow, and knowledge of airflow can be useful to enhance ventilator control and therapy.

This breath sensing technology can, however, still be improved. Sensors that are in the airway of the patient can be prone to problems stemming from tissue interaction, patient-to-patient variability, variability within a given patient over time, variable outside environmental conditions such as temperature and humidity, and variable internal physiological conditions. For example, secretions in the airway could collect on the sensor and could cause signal artifacts and disrupt the sensor's ability to accurately and reliably measure the entire breath curve. Or, the sensor could come into contact with the tracheal wall which would disrupt the sensor's signal. In summary, existing systems have the one or more of the following disadvantages that require improvement: (1) they do not measure the complete breath cycle, (2) they are in-line with the channel used for ventilation gas delivery, (3) they have a limited reliability and robustness, and (4) do not provide an adequate determination of flow which can be useful for enhancing ventilator functions and optimizing therapy.

Therefore, the subject of this invention is to provide improved solutions to intra-airway thermal breath sensing.

SUMMARY OF THE INVENTION

The current invention is an improvement over existing breath sensing techniques for monitoring respiration and controlling ventilator functions. The invention may include temperature responsive breath sensors positioned in the airway or in proximity to an opening of the airway, in parallel with a ventilation circuit and in series with spontaneous airflow flowing in and out of a patient airway. Novel apparatus and methods for protecting and maintaining the sensor signal are also disclosed.

Various techniques for thermal-based breath sensing are described herein. In an exemplary embodiment, response times may be compared between multiple sensing elements to determine direction of airflow. In an exemplary embodiment, heated thermal-based sensors may be used to create a known and consistent offset and signal phase, so that prevailing temperature conditions due not effect the offset or phase. In an exemplary embodiment, a temperature signal may be converted to a volumetric flow rate or breathing volumes. In an exemplary embodiment, a heat source may be located near the thermal-based sensor or sensors to produce a signal response that consistently corresponds to flow direction. In an exemplary embodiment, a single thermal-based sensor may be used in which the offset value is adjusted to maintain a constant offset so that the signal does not drift due to changing prevailing temperature conditions. In an exemplary embodiment, multiple sensor locations may be used to provide reference and comparison values. In an exemplary embodiment, thermal sensors may be placed in a dedicated sensing lumen within the ventilation tube or catheter. In an exemplary embodiment, thermal-based sensors may be used in conjunction with pressure-based sensors in order to obtain both breathing airflow and breathing pressure.

Improved methods and devices are described for sensing the respiration pattern of a patient and controlling ventilator functions, particularly for use in an open ventilation system. An apparatus for sensing respiration and synchronizing a ventilator to the respiration of a patient is described. The apparatus may include a plurality of thermal breath sensors. At least one of the plurality of thermal breath sensors may be a heated thermal breath sensor. The plurality of thermal breath sensors may have attributes selected from the group consisting of: (1) the plurality of thermal breath sensors are joined in a bridge circuit; (2) the at least one heated thermal breath sensor is heated to maintain a desired baseline temperature compared to ambient temperature; (3) the at least one heated thermal breath sensor is heated using a heat source decoupled from the at least one heated thermal breath sensor; and (4) combinations thereof. The plurality of thermal breath sensors may have configurations selected from the group consisting of: (1) one thermal breath sensor is a sensing sensor and a second thermal breath sensor is an ambient reference sensor; (2) one thermal breath sensor is placed near the entrance to or in an airway, and a second thermal breath sensor is placed away from the airway as an ambient reference sensor; (3) two thermal breath sensors are in communication with spontaneous airflow and are joined in bridge circuit, and a third thermal breath sensor is not in communication with the spontaneous airflow and is a reference sensor; (4) at least one thermal breath sensor is positioned in a conduit that is in communication with spontaneous airflow, wherein the cross-section of the conduit and sensor signal are used to determine a volumetric flow rate; (5) two thermal breath sensors are separated by a barrier to create a directionally biased signal response phase shift between the signals of the two thermal breath sensors, wherein the phase shift directionality is used to determine the direction of airflow and the phase of respiration; and (6) combinations thereof. A DC shift of a signal from at least one of the plurality of thermal breath sensors may be controlled by (1) continually adjusting a source voltage or (2) auto-zeroing through a software feedback loop. The plurality of thermal breath sensors may be selected from the group consisting of: thermistors; polymer based thermally responsive materials; thermally responsive materials shaped like a bead, strip or ring; and combinations thereof. A signal from the plurality of thermal breath sensors may be correlated to flow, and the flow may be correlated to depth of breathing, inspiratory effort, inspiratory and expiratory flow, inspiratory and expiratory volume, and patient respiratory status.

An apparatus may be provided for sensing respiration and synchronizing a ventilator to the respiration of a patient. The apparatus may include at least three thermal breath sensors. A first thermal breath sensor may measure temperature in an airway of the patient, a second thermal breath sensor may measure temperature at or near the opening of an airway of the patient, and a third thermal breath sensor may measure ambient temperature. Signals from the first thermal breath sensor and the second thermal breath sensor may be initially compared to a signal from the third thermal breath sensor to determine if inspired ambient air should be warmer or cooler than body temperature, and wherein the initial signal comparison defines an inspiratory phase and an expiratory phase associated with the signals from the first thermal breath sensor and the second thermal breath sensor. The signals from the first thermal breath sensor and the second thermal breath sensor are subsequently compared to each other to compensate for drift and artifacts, and wherein the subsequent signal comparison is used to determine true patterns, phases and timing of the patient's respiration. The at least three thermal breath sensors may have attributes selected from the group consisting of: (1) the first thermal breath sensor and the second thermal breath sensor are joined in a bridge circuit; (2) at least one of the first thermal breath sensor and the second thermal breath sensor are heated to maintain a desired baseline temperature compared to ambient temperature; (3) at least one of the first thermal breath sensor and the second thermal breath sensor are heated using a heat source decoupled from the at least one of the first thermal breath sensor and the second thermal breath sensor; and (4) combinations thereof. The at least three thermal breath sensors may have configurations selected from the group consisting of: (1) the first thermal breath sensor and the second thermal breath sensor are in communication with spontaneous airflow and are joined in a bridge circuit, and the third thermal breath sensor is not in communication with spontaneous airflow and is a reference sensor; (2) at least one of the at least three thermal breath sensors is positioned in a conduit that is in communication with spontaneous airflow, wherein the cross-section of the conduit and sensor signal are used to determine a volumetric flow rate; (3) the first thermal breath sensor and the second thermal breath sensor are separated by a barrier to create a directionally biased signal response phase shift between the signals of the first thermal breath sensor and the second thermal breath sensor, wherein the phase shift directionality is used to determine the direction of airflow and the phase of respiration; and (4) combinations thereof. A DC shift of a signal of at least one of the at least three thermal breath sensors may be controlled by (1) continually adjusting a source voltage or (2) auto-zeroing through a software feedback loop. The at least three thermal breath sensors may be selected from the group consisting of: thermistors; polymer based thermally responsive materials; thermally responsive materials shaped like a bead, strip or ring; and combinations thereof. A signal from one or both of the first thermal breath sensor and the second thermal breath sensor may be correlated to flow, and the flow may be correlated to depth of breathing, inspiratory effort, inspiratory and expiratory flow, inspiratory and expiratory volume, and patient respiratory status.

An apparatus may be provided for sensing respiration and synchronizing a ventilator to the respiration of a patient. The apparatus may include a ventilation tube to deliver gas to the patient, where the ventilation tube further includes a ventilation gas delivery channel to deliver gas to the patient. A breath sensing conduit may be in communication with an airway of the patient, where a thermal breath sensor is positioned in series with the breath sensing conduit. The thermal breath sensor may have attributes selected from the group consisting of: (1) the thermal breath sensor is joined with a second sensor in a bridge circuit; (2) the thermal breath sensor is heated to maintain a desired baseline temperature compared to ambient temperature; (3) the thermal breath sensor is heated using a heat source decoupled from the thermal breath sensor; and (4) combinations thereof. The apparatus may have configurations selected from the group consisting of: (1) the apparatus includes a second sensor that is an ambient temperature reference sensor; (2) the thermal breath sensor is placed near the entrance to an airway; (3) the thermal breath sensor is placed in an airway; (4) the thermal breath sensor is positioned in the sensing conduit near or in the patient's airway; and (5) combinations thereof. A DC shift of a signal of the thermal breath sensor may be controlled by (1) continually adjusting a source voltage or (2) auto-zeroing through a software feedback loop. The thermal breath sensor may be selected from the group consisting of: thermistors; polymer based thermally responsive materials; thermally responsive materials shaped like a bead, strip or ring; and combinations thereof. A signal from the thermal breath sensor may be correlated to flow, and the flow may be correlated to depth of breathing, inspiratory effort, inspiratory and expiratory flow, inspiratory and expiratory volume, and patient respiratory status. A signal from the thermal breath sensor may be correlated to flow using the signal and a cross sectional area of the sensing conduit, and the flow may be correlated to depth of breathing, inspiratory effort, inspiratory and expiratory flow, inspiratory and expiratory volume, and patient respiratory status. An intra-airway pressure sensing conduit may be provided, where at least one thermal breath sensor may be used to determine spontaneous breathing airflow, and the intra-airway pressure sensing conduit may be used to determine breathing pressure.

In certain embodiments, a method for breath sensing and controlling a ventilator may use two sensing systems, a thermal sensor for measuring tracheal airflow and a pressure sensor for measuring tracheal pressure. In certain embodiments, a method for breath sensing and controlling a ventilator may use two temperature sensitive elements where one element is exposed to ambient temperature and the other element is placed in the airway exposed to the intratracheal temperature. A method for breath sensing and controlling a ventilator may use three temperature sensitive elements, where one element is placed at the breathing entry point, for example the nose or mouth, and the other element is exposed to ambient temperature and the other element is placed in the airway exposed to the intratracheal temperature. A method and apparatus for sensing breathing and controlling a ventilator may use an array of temperature sensitive elements and comparing the temporal differences in the signals of the different elements to derive airflow direction and speed. A method and apparatus for sensing breathing and controlling a ventilator may use heated temperature-sensitive elements, and comparing the temporal differences in the signals. A method and apparatus for sensing breathing and controlling a ventilator may use a pair of temperature-sensitive elements arranged in a Wheatstone bridge, with one element heated. A method and apparatus for sensing breathing and controlling a ventilator may use a pair of temperature-sensitive elements arranged in a Wheatstone bridge, and while heating the pair of elements. A method for breath sensing and controlling a ventilator may use two temperature sensitive elements, with a heat source located near the elements. A method for breath sensing and controlling a ventilator may use two temperature sensitive elements arranged in a Wheatstone bridge configuration with a heat source located near the elements. A method for breath sensing and controlling a ventilator may use a single temperature sensitive element where the DC shift of the signal of the element is controlled by continually adjusting the source voltage or by auto-zeroing through software feedback loop. A method for breath sensing and controlling a ventilator may use a temperature sensitive element placed in an auxiliary sensing lumen in the gas delivery circuit. A method for breath sensing and controlling a ventilator may use a pair of temperature sensitive elements placed in an auxiliary sensing lumen in the gas delivery circuit, and optionally arranged in a Wheatstone bridge. A method for breath sensing and controlling a ventilator may use an array of sensing elements placed the trachea, the gas delivery circuit main lumen, and an auxiliary sensing lumen in the gas delivery circuit. A method and apparatus for sensing breathing and controlling a ventilator may use temperature-sensitive elements contained in a channel of known cross section, the signal from the elements used to determine airflow speed and volume using the known cross sectional dimension. A method and apparatus for sensing breathing and controlling a ventilator may use two sensing elements with a physical screen between the elements to bias the response time of each element due to the direction of flow. A method and apparatus for sensing breathing and controlling a ventilator may use two sensing elements on the inferior and superior aspects of the delivery cannula to create a physical barrier to bias the response time of each element that correlates to the direction of flow. A method and apparatus for sensing breathing and controlling a ventilator may use a inner and outer delivery cannula with an annular space between the inner and outer cannula and with a valve allowing for inspiratory flow through the annular space from ambient air but disallowing expiratory flow, and wherein a thermal breath sensing element placed in the annular space between the inner and outer cannula. A method and apparatus for sensing breathing and controlling a ventilator may use thermally sensitive sensing elements disposed in the airway. A method and apparatus for sensing breathing and controlling a ventilator may use thermally sensitive sensing elements disposed outside the airway. A method and apparatus for sensing breathing and controlling a ventilator may use thermally sensitive sensing elements disposed both inside and outside the airway. A method and apparatus for sensing breathing and controlling a ventilator may use thermally sensitive sensing elements disposed in a flow path between a two piece inner and outer ventilation tube. A method and apparatus for sensing breathing and controlling a ventilator may use thermally sensitive sensing elements disposed in a flow path between a stoma sleeve and a ventilation tube placed through the stoma sleeve. A method and apparatus for sensing breathing and controlling a ventilator may use thermally sensitive sensing elements disposed in the airway and comprising a flush system to delivery a fluid to the sensor to flush away debris. The flush system may flush the sensor continuously, intermittently, or when the sensor signal fades due to debris. The temperature sensitive element may be a thermistor. The temperature sensitive element may be a polymer based thermally responsive material. The sensing element may be a bead, a strip or a ring. The sensing element may be protected by a shield. The sensing element may be disposed in the inferior, superior, anterior, posterior or lateral sides of the ventilation tube, or combinations thereof. The pressure and flow data may be used to determine airway resistance, lung compliance, and an estimate of work of breathing. The ventilation tube may include an inflatable and deflatable cuff, and at least two sensing lumens with one lumen terminating distal to the cuff and one lumen terminating proximal to the cuff, wherein the pressures of the two sensing lumens are compared to provide an indication of the degree of obstruction being caused by the cuff.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF THE INVENTION

The accompanying drawings, which are included to provide a further understanding of the invention and are incorporated in and constitute a part of this specification, illustrate preferred embodiments of the invention and together with the detailed description serve to explain the principles of the invention. In the drawings:

FIG. 4A shows graphically conventional breath sensing.

FIG. 4B shows graphically breath sensing described in this invention.

FIG. 4C shows graphically chest impedance breath sensing.

FIG. 5 shows breath sensing using an array of temperature sensitive elements and comparing the temporal differences in the signals of the different elements to derive airflow direction and speed.

FIG. 5A shows graphically the signal tracings from the sensors of FIG. 5 indicating the temporal difference used to distinguish inspiration from exhalation.

Figure 7:
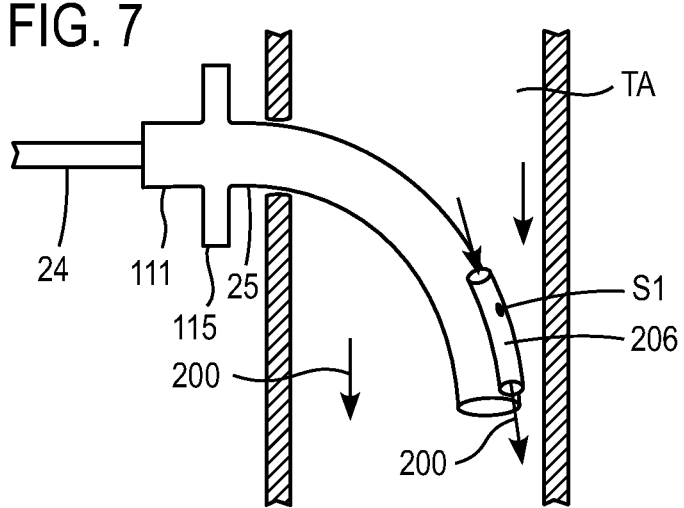
FIG. 7 shows breath sensing using temperature-sensitive elements contained in a conduit of known cross section used to correlate the signal to airflow speed and volume using the known cross sectional dimension.
Figure 7A:
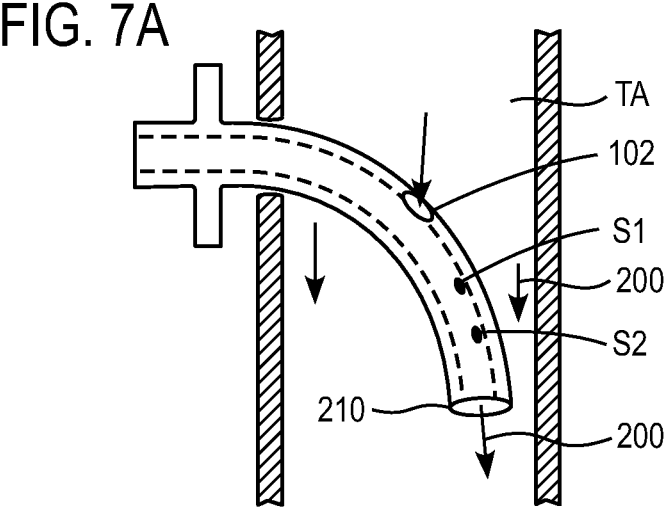

FIG. 7A describes an alternate configuration to that shown in FIG. 7 in which the sensors are placed inside a channel of a ventilation tube, with the channel acting as the flow conduit.

Figure 7B:
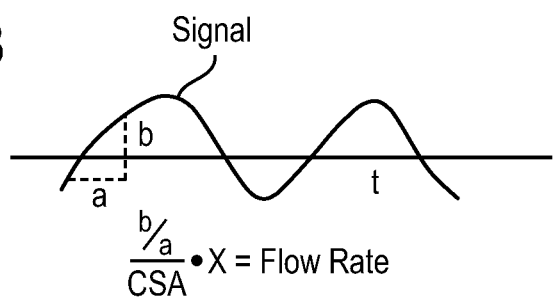

FIG. 7B shows the resultant signals of the system of FIG. 7 used to compute flow rate.

Figure 8:
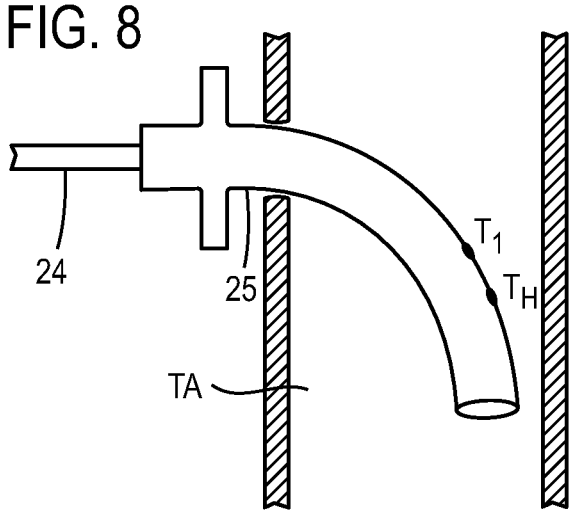

FIG. 8 shows breath sensing using a pair of temperature-sensitive elements arranged in a Wheatstone bridge, with one element heated.

Figure 8A:
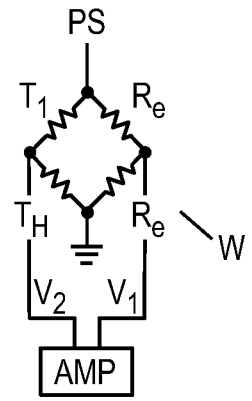

FIG. 8A shows the bridge circuit of the sensor array shown in FIG. 8.

FIG. 8B shows the resultant signals of the sensing elements of FIG. 8.

FIG. 9 shows breath sensing using a pair of temperature-sensitive elements arranged in a Wheatstone bridge, and while heating the pair of elements.

FIG. 9A shows the sensor signal tracings from the sensing elements shown in FIG. 9, before and after the elements are heated.

FIG. 9B shows the sensor signal tracing of the bridge output signal of the sensor array shown in FIG. 9, at a high and low ambient temperature, indicating similar bridge output amplitude and offset regardless of ambient temperature conditions.

Figure 10:
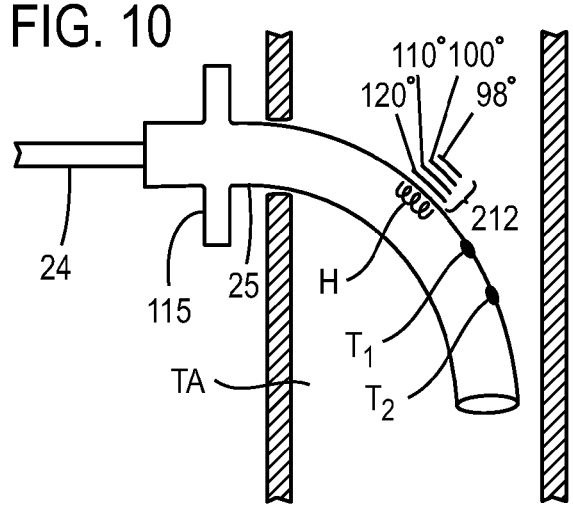

FIG. 10 shows breath sensing using two temperature sensitive elements, with a heat source located near the elements.

Figure 10A:
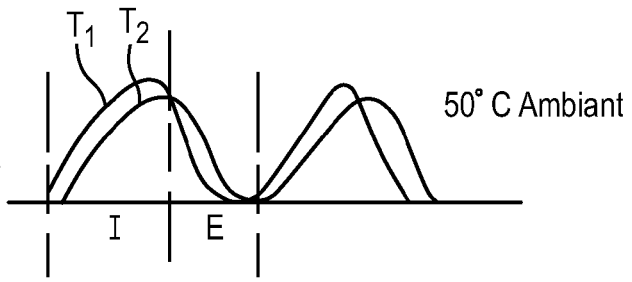

FIG. 10A shows the sensor signal tracings at a high ambient temperature condition of the sensing system shown in FIG. 10.

Figure 10B:
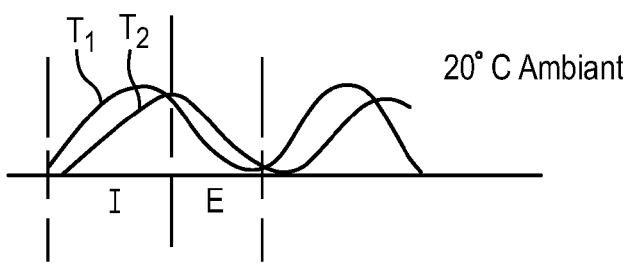

FIG. 10B shows the sensor signal tracings at a low ambient temperature condition of the sensing system shown in FIG. 10.

Figure 11:
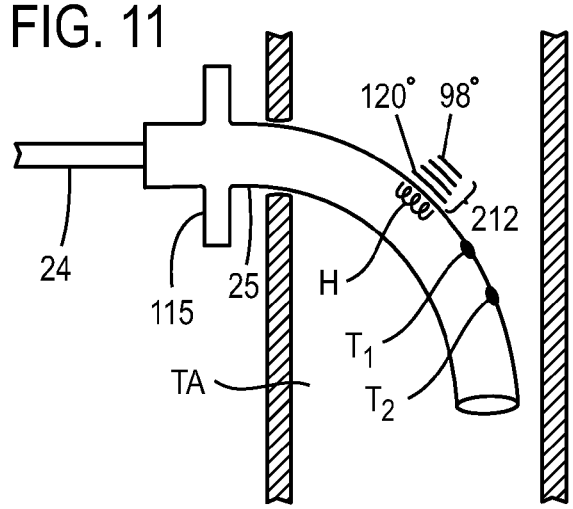

FIG. 11 shows breath sensing using two temperature sensitive elements arranged in a Wheatstone bridge configuration with a heat source located near the elements.

FIG. 11A shows the bridge output signal and the differential over time of the bridge output signal of the sensing system shown in FIG. 11.

FIG. 12 shows breath sensing using a single temperature sensitive element where the DC shift of the signal of the element is controlled by continually adjusting the source voltage or by auto-zeroing through software feedback loop.

FIG. 12A shows the circuit diagram of the sensing system described in FIG. 12.

FIG. 12B shows the signal tracing of the sensor described in FIG. 12, without compensation for drift.

FIG. 12C shows the signal tracing of the sensor described in FIG. 12, with compensation for drift.

FIG. 12D describes an alternative to the sensing system of FIG. 12 in which the sensing element is heated.

FIG. 12E describes an alternative to the sensing system of FIG. 12 in which the sensor is configured in an electrical bridge circuit.

Figure 13:
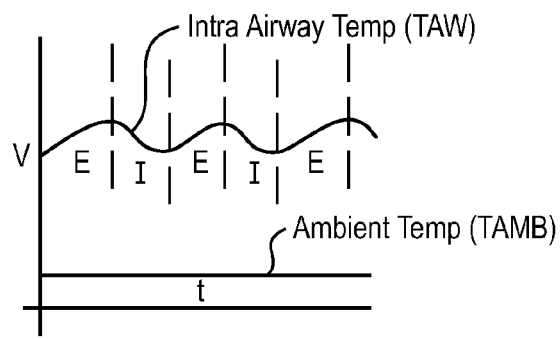

FIG. 13 shows a graphical representation of breath sensing using two temperature sensitive elements where one element is exposed to ambient temperature and the other element is placed in or in proximity to an airway and exposed to airway temperature, and the comparison provides breath phase information.

Figure 13A:
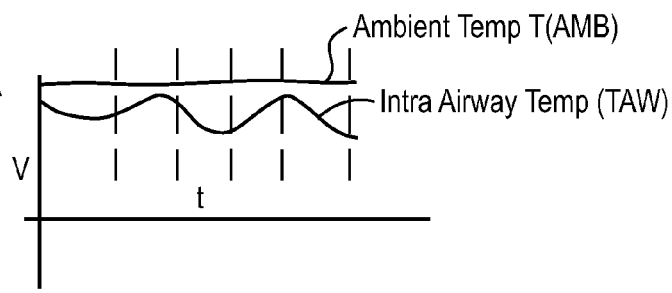

FIG. 13A shows the system of FIG. 13 in which the ambient temperature is greater than body temperature indicating that a decreasing signal of the airway temperature sensor indicates exhalation phase.

FIGS. 14A-D shows breath sensing using three temperature sensitive elements, where one element is placed at the breathing entry point, for example the nose or mouth, and the other element is exposed to ambient temperature and the other element is placed in the airway exposed to the intratracheal, intra-oral, or intra-nasal temperature.

Figure 14A:
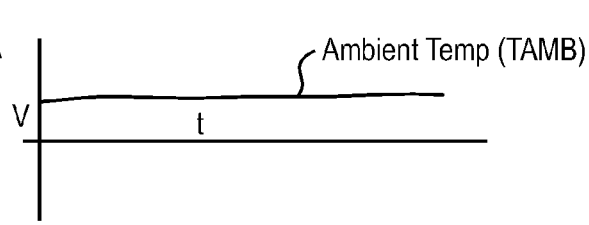
Figure 14B:
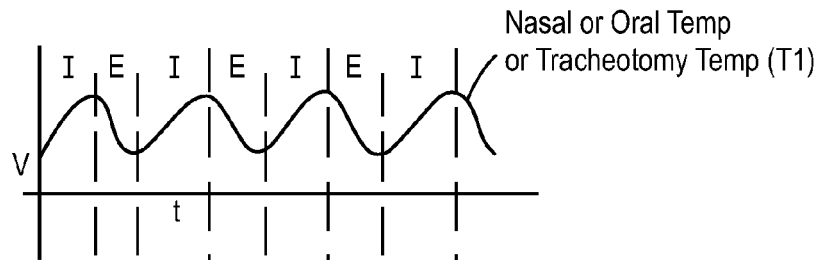
Figure 14C:
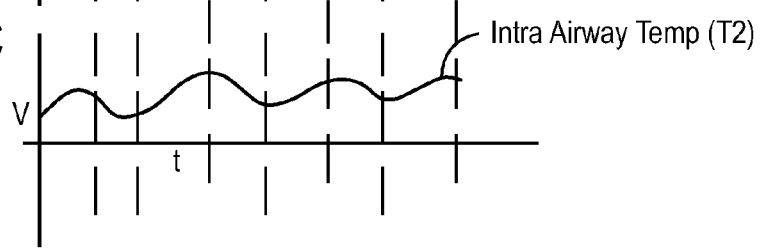
Figure 14D:
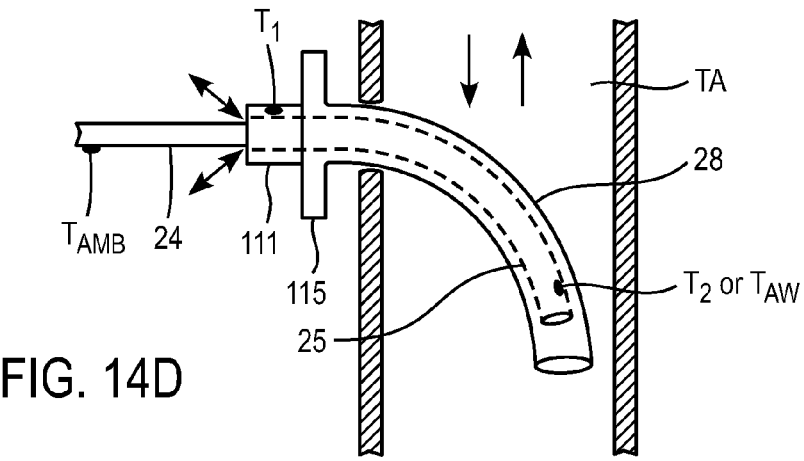

FIG. 14A shows the ambient sensing signal tracing of the system shown in FIG. 14D.

FIG. 14B shows the nasal, oral or tracheotomy sensing signal tracing of the system shown in FIG. 14D.

FIG. 14C shows the intra-tracheal, intra-nasal, or intra-oral sensor signal tracing of the system shown in FIG. 14D.

FIG. 14D shows the patient interface configuration indicating an ambient sensor, an intra-airway sensor, and a proximal airway sensor positioned near the airway entrance.

Figure 15:
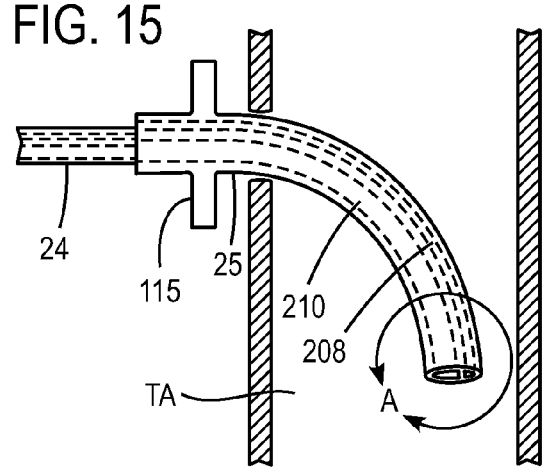

FIG. 15 shows breath sensing using a temperature sensitive element placed in an auxiliary sensing lumen in the gas delivery circuit.

Figure 15A:
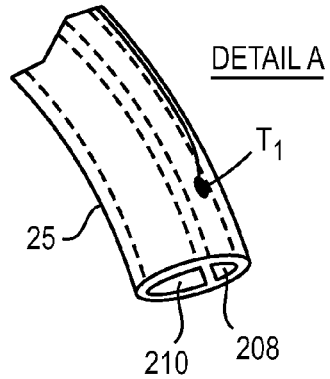

FIG. 15A shows a detailed view of location A of the interface shown in FIG. 15, indicating the sensing element positioned in a sensing channel.

Figure 15B:
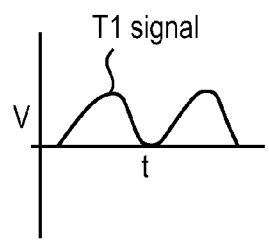

FIG. 15B shows graphically the signal tracing from the sensor of FIG. 15.

Figure 16:
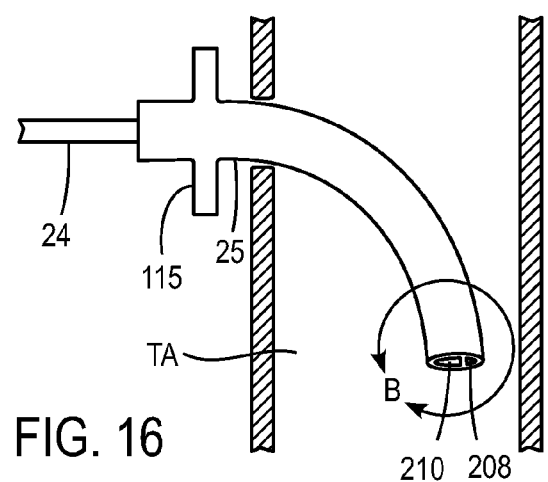

FIG. 16 shows breath sensing using a pair of temperature sensitive elements placed in an auxiliary sensing lumen in the gas delivery circuit, and optionally arranged in a Wheatstone bridge.

Figure 16A:
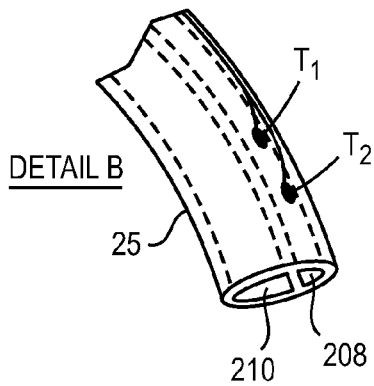

FIG. 16A shows a detailed view of location B of the interface shown in FIG. 16, indicating the sensing element positioned in a sensing channel.

Figure 16B:
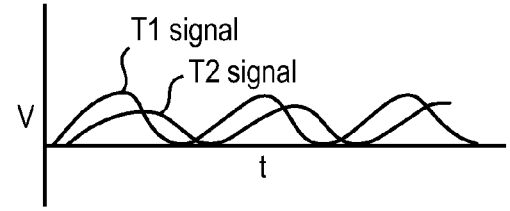

FIG. 16B shows graphically the signal tracings from the two sensing elements of FIG. 16, indicating a phase shift and amplitude difference between the two signals.

Figure 17:
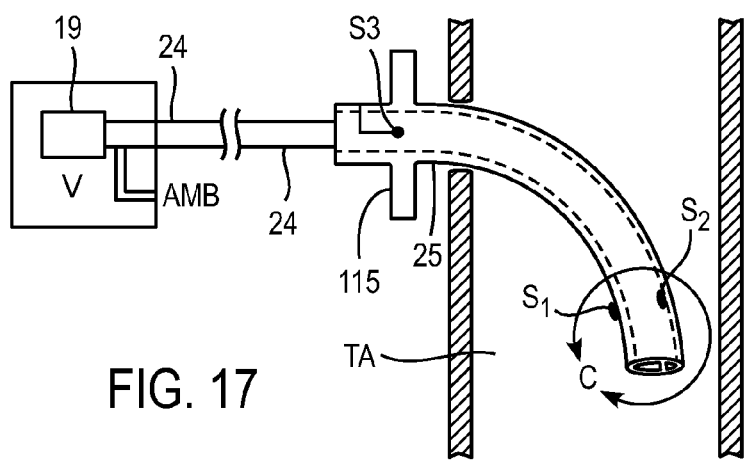

FIG. 17 shows breath sensing using combinations of sensing elements placed the trachea, the gas delivery circuit main lumen, and an auxiliary sensing lumen in the gas delivery circuit.

Figure 17A:
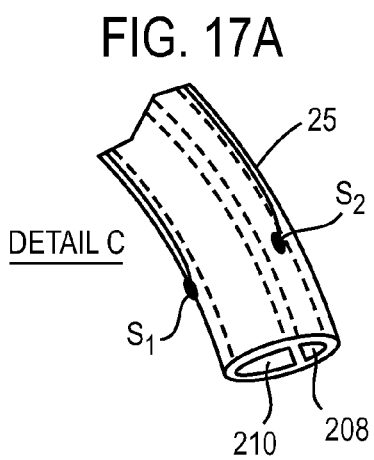

FIG. 17A shows a detailed view of area C of FIG. 17.

Figure 17B:
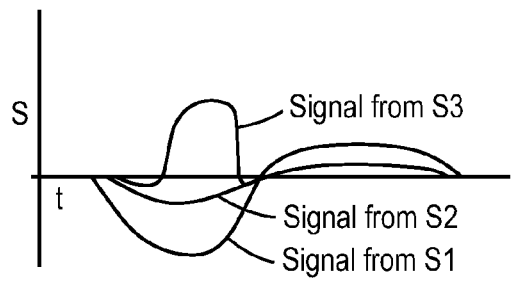

FIG. 17B shows graphically the signal tracings from the sensing elements shown in FIG. 17.

Figure 18:
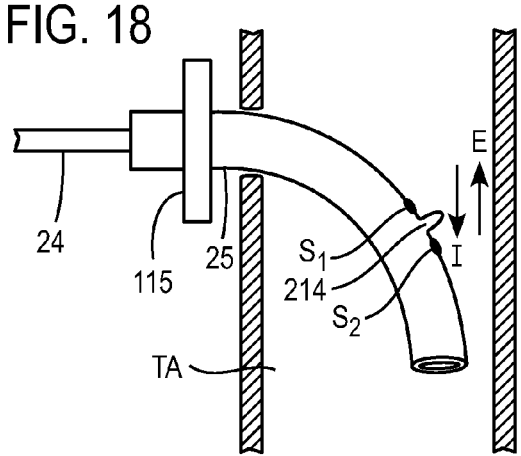

FIG. 18 shows breath sensing using two sensing elements with a physical screen between the elements to bias the response time of each element due to the direction of flow.

Figure 18A:
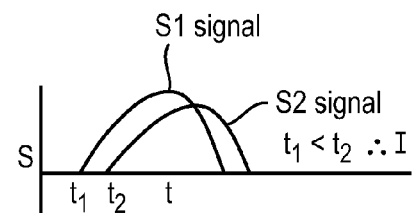

FIG. 18A shows the signal tracings of the sensors of FIG. 18 in which the phase shift indicates inspiratory phase.

Figure 18B:
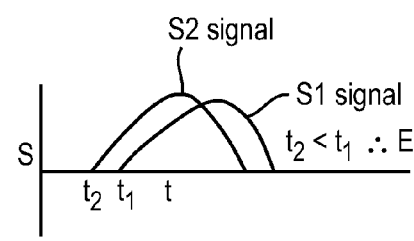

FIG. 18B shows the signal tracings of the sensors of FIG. 18 in which the phase shift indicates expiratory phase.

Figure 19:
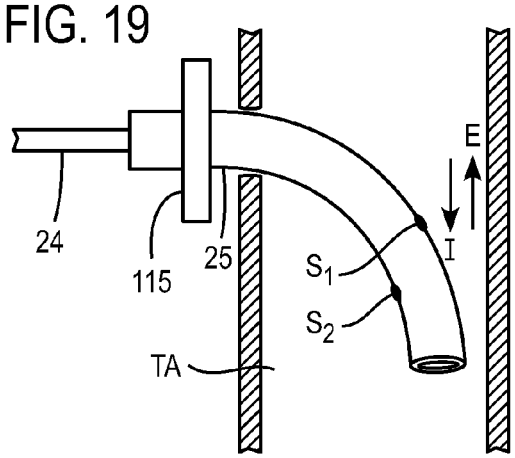

FIG. 19 shows breath sensing using two sensing elements on the inferior and superior aspects of the delivery cannula to create a physical barrier to bias the response time of each element that correlates to the direction of flow.

Figure 19A:
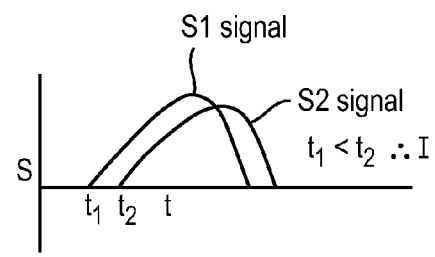

FIG. 19A shows the signal tracings of the sensors of FIG. 18 in which the phase shift indicates inspiratory phase.

Figure 19B:
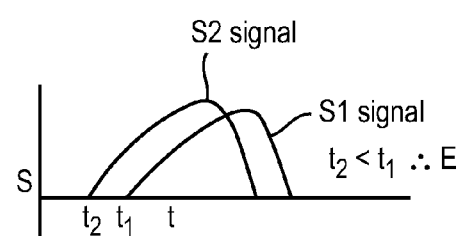

FIG. 19B shows the signal tracings of the sensors of FIG. 18 in which the phase shift indicates expiratory phase.

Figure 20:
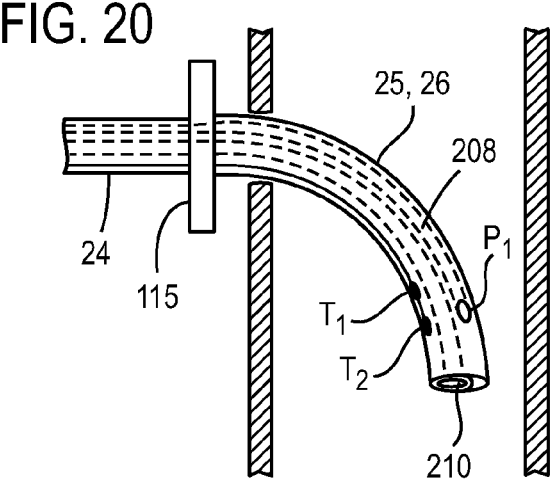

FIG. 20 shows breath sensing using two sensing systems, a thermal sensor for measuring tracheal airflow and a pressure sensor for measuring tracheal pressure.

Figure 20A:
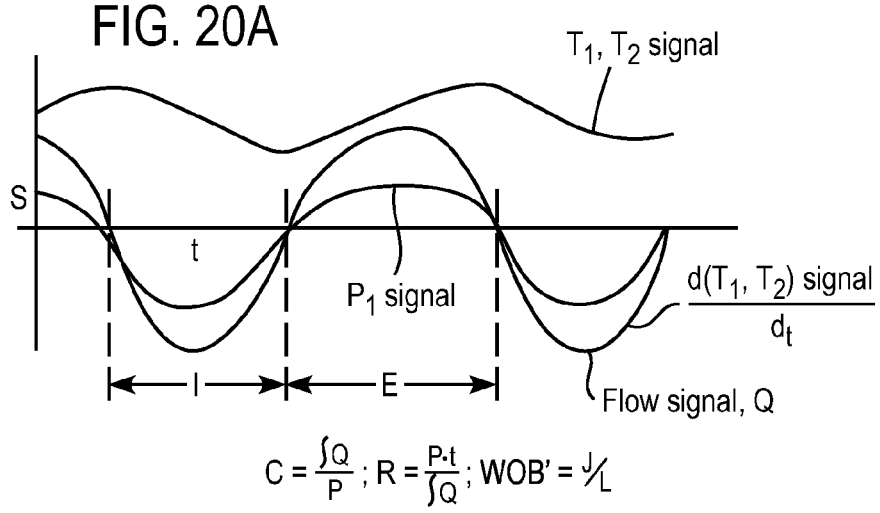

FIG. 20A shows resultant flow and pressure signals for the system described in FIG. 20, showing determination of compliance, resistance and a surrogate for work of breathing.

Figure 21:
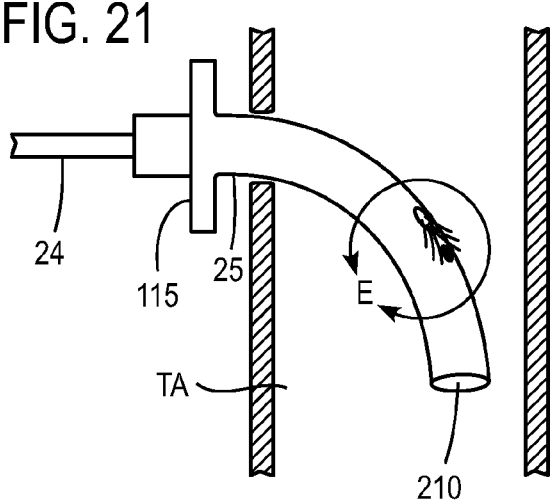

FIG. 21 shows breath sensing using an intra-airway sensor and a flush lumen and flush port in the delivery tube to maintain a contamination-free sensor.

Figure 21A:
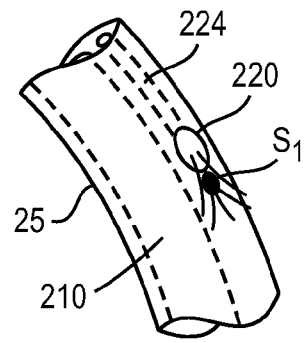

FIG. 21A shows a detailed view of area E of FIG. 21.

Figure 22:
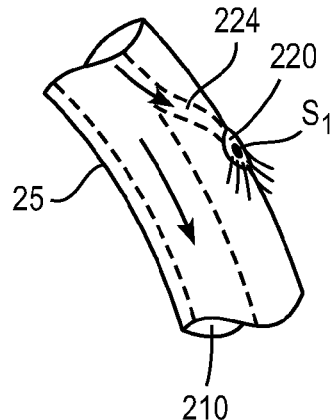

FIG. 22 shows breath sensing using an intra-airway sensor and a flush port connected to the gas delivery channel to maintain a contamination-free sensor.

Figure 23A:
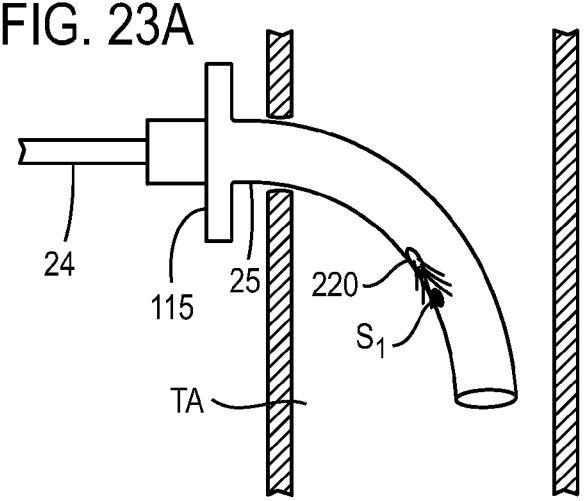

FIG. 23A shows an alternate location of the flush port described in FIG. 21, wherein the sensor and flush port are located on the anterior or inferior side of the ventilation tube.

Figure 23B:
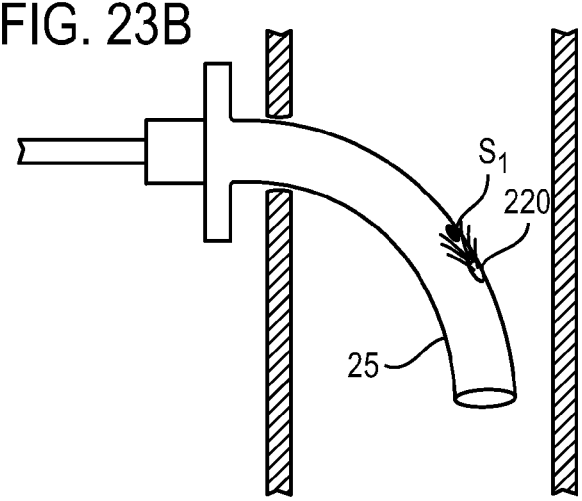

FIG. 23B shows an alternative configuration of the flush port described in FIG. 21, wherein the sensor and flush port are located on the posterior or superior surface of the ventilation tube and the flush port is positioned so that the flush media is directed in a retrograde direction at the sensor.

Figure 24A:
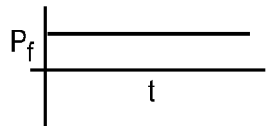

FIG. 24A shows a graphical description of a constant steady state flushing pressure profile.

Figure 24B:
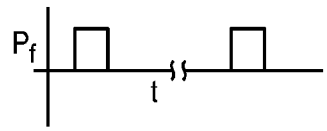

FIG. 24B shows a graphical description of an intermittent flushing pressure profile in which flushing occurs as needed or intermittently.

Figure 24C:
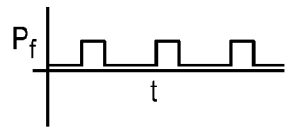

FIG. 24C shows a graphical description of a cyclical flushing pressure profile, optionally in synchrony with the patient's respiration pattern.

Figure 25:
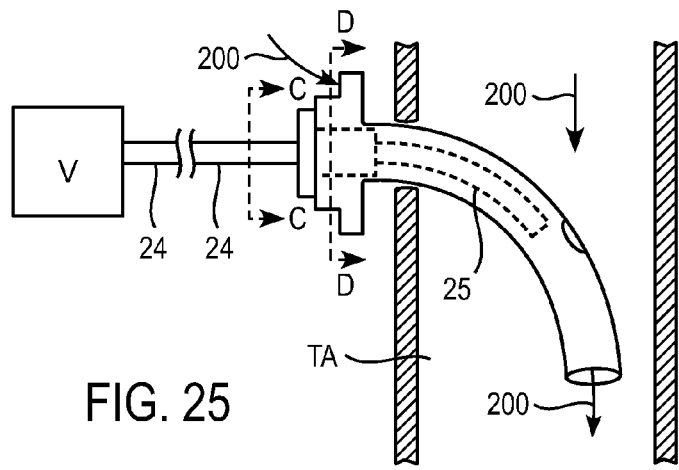

FIG. 25 shows breath sensing and ventilation system in which a ventilation tube is placed into a outer sleeve, such as a tracheostomy tube, stomal guide, nose guide or oral guide, with breath sensors, and optionally a heat moisture exchanger, bacterial filter, and breathing port and inspiratory valve positioned in the annular space between the tube and outer sleeve.

Figure 25A:
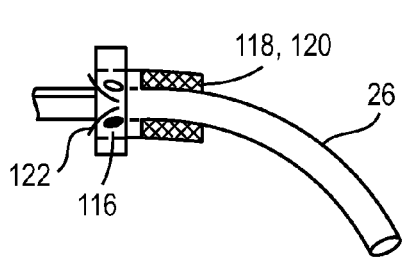

FIG. 25A shows the ventilation tube of FIG. 25.

Figure 25B:
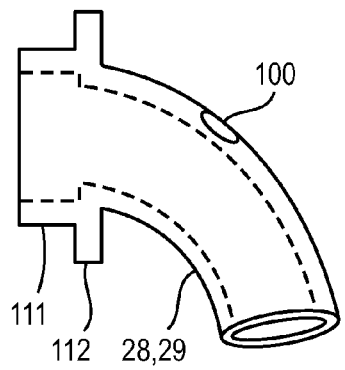

FIG. 25B shows the outer sleeve of FIG. 25.

Figure 25C:
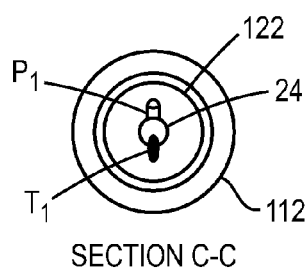

FIG. 25C shows a cross sectional view through line C-C of FIG. 25.

Figure 25D:
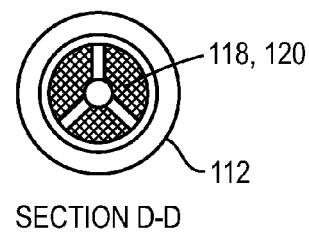

FIG. 25D shows a cross sectional view through line D-D of FIG. 25.

DETAILED DESCRIPTION OF THE PREFERRED EMBODIMENTS

Figure 1:
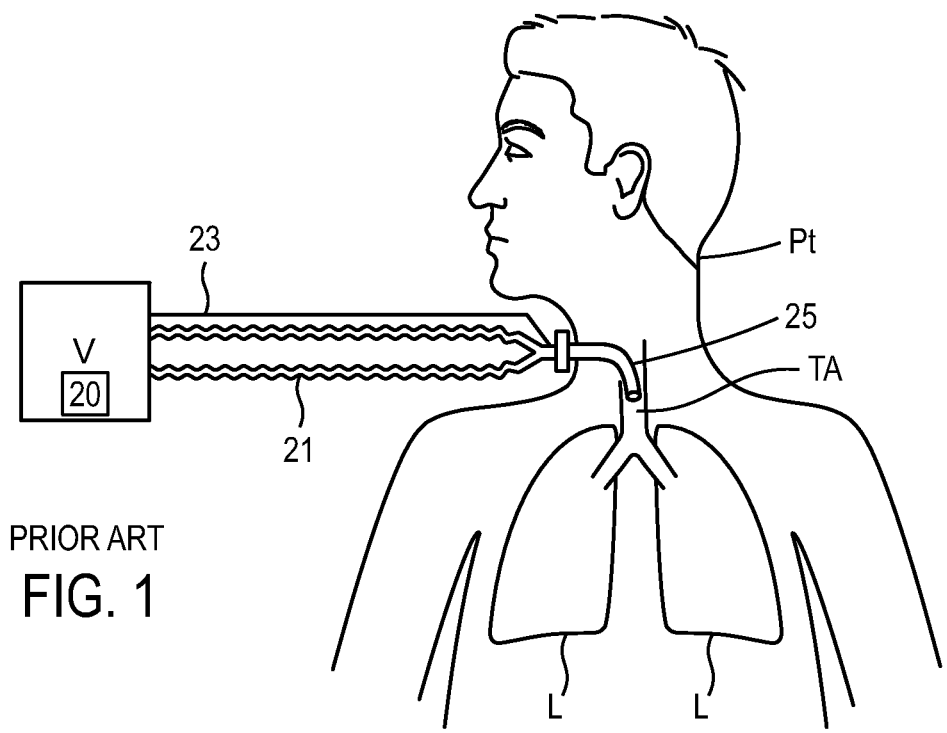
FIG. 1 shows prior art breath sensing in series with breathing circuit for ventilator control.
Figure 1A:
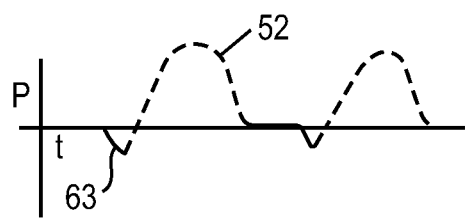
FIG. 1A shows graphical representation of the respiration signal masked by the ventilator gas delivery pressure.

FIG. 1 (prior art) describes a conventional ventilator system in which the breath sensor is in line with the ventilation gas being delivered in the breathing circuit. The Ventilator V delivers gas to the patient Pt through the ventilation gas delivery circuit, dual limb 21 and ventilation tube 25. A pressure tap 23 in series or in line with the ventilator gas flow senses a negative pressure created by a patient inspiratory effort. Alternatively, a flow sensor can be used in series with the ventilation circuit to detect when the patient inspires. The signal from the breath sensor is delivered to a ventilator control unit 20 in the ventilator V. As seen in FIG. 1A these in-series sensor systems measure the start of a patient inspiratory effort 63, but after the ventilator V is triggered to deliver a mechanical breath to the patient Pt, the sensor signal predominantly indicates the ventilator activity in the form of a ventilator gas delivery pressure tracing 52, and not the patient activity.

Figure 2:
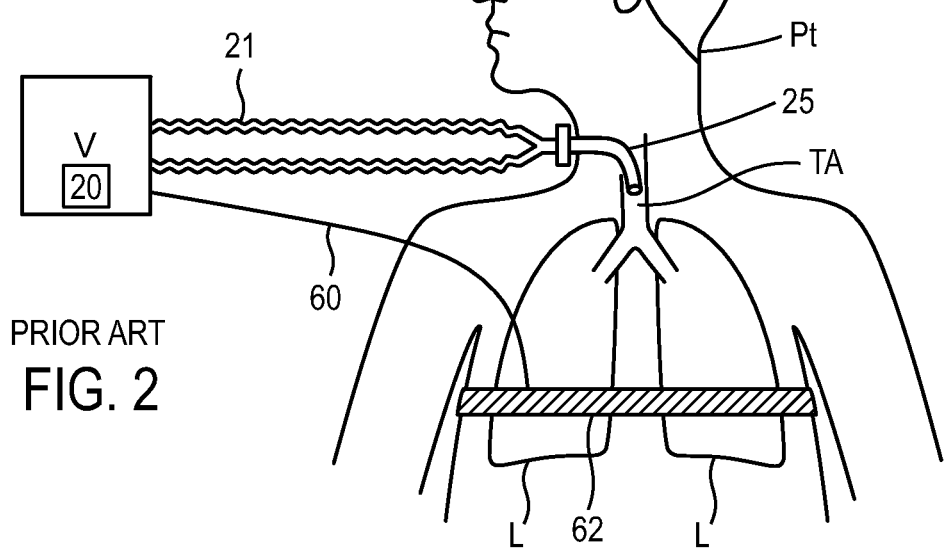
FIG. 2 shows prior art breath sensing for ventilator control using chest impedance.
Figure 2A:
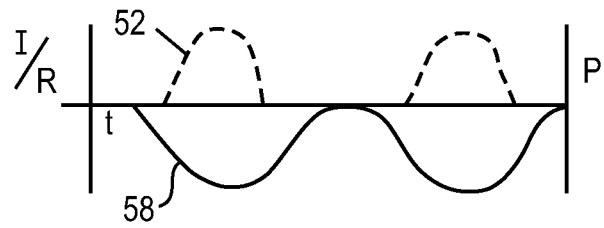
FIG. 2A shows a graphical representation of the ventilation gas delivery pressure and the respiration sensor signal.

FIG. 2 describes a ventilator breath sensing triggering system in which the breath sensor is a chest impedance sensor system, as described in U.S. Publication No. 2005/0034721. In this case, the sensor is placed in parallel with the ventilation circuit. A chest impedance band 62 is connected to the ventilator V control unit 20 by chest impedance wires 60. As shown in FIG. 2A, the patient spontaneous respiration curve 58 is not masked by the pressure waveform in the ventilator gas delivery pressure tracing 52. Although an improvement over prior art, the impedance sensor can have a tendency to register motion of the person which is not related to breathing and hence can include artifacts.

Figure 3:
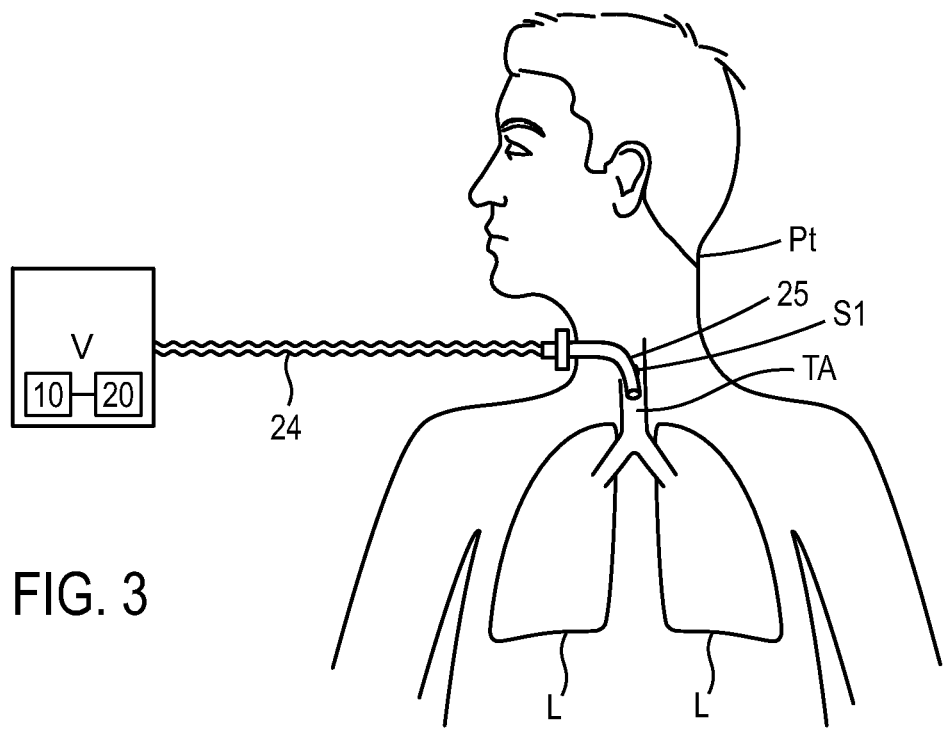
FIG. 3 shows intra-airway breath sensing for ventilator control.
Figure 3A:
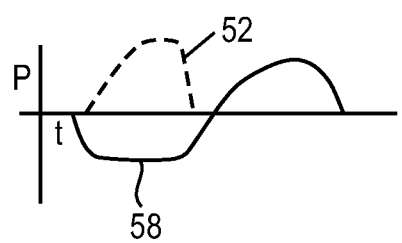
FIG. 3A shows graphical representation of the ventilation gas delivery pressure and the respiration sensor signal.

FIG. 3 describes an overall configuration of an embodiment of the present invention, including a ventilator V, a ventilation gas delivery circuit, single limb 24, ventilation tube 25 and sensor or pressure sensing port S1 positioned to measure intra-airway tracheal air flow or breathing pressures or nasal or oral air flow, positioned inside or near the airway. While the following exemplary embodiments are described for intra-airway tracheal air flow, similar concepts may apply to nasal and oral air flow. The breath sensor or sensing port S1 may be an intra-tracheal sensor, conduit or port located in the tracheal airway TA in the path of the patient's airflow, and in parallel with the ventilation circuit 24. The sensor, conduit or sensing port is typically but not always part of or attached to the ventilation tube 25. The signal may be delivered to the ventilator control unit 20 by means of wires or sensing conduits, or alternate transmission means such as fiber optic or wireless. The ventilator V may have one or more processors 10 for receiving and analyzing signals from the sensors. The processor 10 may process receive and process signals from the sensors and compute relevant parameters as described below. The processor 10 may then output the signals and/or the results of computations. The processor 10, ventilator V, and/or ventilator control unit 20 may then output the signals, the results of the analyzing and/or control ventilation based upon the analysis. As seen in FIG. 3A, this may be an improvement over conventional in-series breath sensing systems in that the actual breathing signal 58 is not masked by the ventilation gas delivery pressure signal 52, and the sensor measures both the patient's true breathing activity 58 as well as the effect that the ventilation gas delivery has on the patient's lung pressure and airway breath flow. This is especially important in open ventilation systems. Also, as will be explained in later sections, the present invention describes improvements related to signal drift, artifacts, and disturbance caused by patient movement and changing temperature conditions.

It should be noted that while in FIG. 3 and in the following descriptions, the sensing system is typically described in conjunction with a transtracheal ventilation catheter, the transtracheal ventilation catheter is exemplary only and other interfaces are included in the invention, such as but not limited to: a trans-nasal catheter, a trans-oral catheter, transtracheal tube catheters, percutaneous catheters, oral cannula, nasal cannula, non-invasive mask oral and/or nasal interfaces, open nasal and open oral cannula interfaces. For simplicity, the following embodiments are typically described with a transtracheal catheter; however the invention is also applied to the other interfaces stated above.

FIGS. 4A-C graphically describes the difference between using intra-airway sensors which directly measure tracheal airflow and respiration, versus conventional in-line ventilator sensing systems. FIG. 4A describes a conventional system in which the flow sensor measures a patient inspiratory effort 63 but then measures the ventilator gas flow 52. As one example of the disadvantages of this conventional system, the resultant inspiratory time determined by the ventilator is the inspiratory time set by the user on the ventilator, and not the true patient's spontaneous inspiratory time determined by a spontaneous breathing sensor, and for example as a result the patient's exhalation curve 66 begins later than the patient's true start of exhalation. FIG. 4B describes mechanical augmented ventilation in which airway airflow is measured at all times, hence during the period of ventilation gas delivery, the waveform accurately shows the combined effect in the lung or airway of spontaneous breathing and artificial ventilation. FIG. 4C shows a system with a chest impedance sensor which shows an artificial trigger of the ventilator gas delivery 52 due to an artifact in the signal 77 occurring before the true start of inspiration.

In FIG. 5, two thermal sensing elements Tp, Td may be positioned on a ventilation tube 25 and spaced apart by a distance. As seen in FIG. 5A, the phase of the two signals defined by the difference between t1 and t2 may be compared to determine direction of airflow. During inspiration, the proximal thermistor Tp may respond to a change in temperature slightly sooner than the distal thermistor Td. By comparing the temporal differences in the inflection points of the two signals, the direction of airflow may be determined. For example, if the proximal sensor signal is seen to respond sooner than the distal sensor signal, it can be deduced that the airflow is moving in the inspiratory direction, and the sensing algorithms may declare that portion of the breath waveform as inspiration 200. If the proximal sensor signal is seen to respond later than the distal sensor signal, it can be deduced that the airflow is moving in the expiratory direction, and the sensing algorithms may declare that portion of the breath waveform as expiration 202. Ventilator gas flow 204 may pass through a ventilation gas delivery circuit, a ventilation catheter flange, and the ventilation tube 25.

Figure 6:
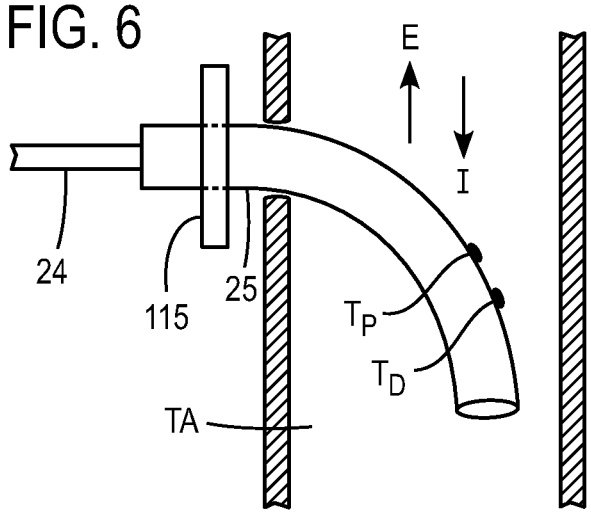
FIG. 6 shows breath sensing using heated temperature-sensitive elements, and comparing the temporal differences in the signals.
Figure 6A:
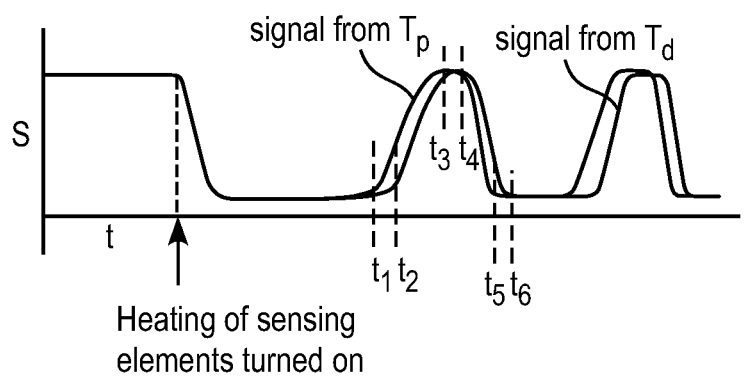
FIG. 6A shows graphically the signal tracings from the sensors of FIG. 6 indicating the resultant signal when the sensor elements are heated.

In FIG. 6, a transtracheal tube is described similar to that described in FIG. 5 except the temperature sensing elements Tp, Td are heated at a time $t_h$, as indicated by the arrow in FIG. 6A, to a desired temperature that may always be higher than the possible conditions encountered in the patient Pt. In this case, the signal of the sensor during iso-flow conditions to the right of $t_h$ is maintained at a constant level regardless of patient temperature or ambient temperature. This may be in contrast to the non-heated case in FIG. 5 where the sensor signal can shift even during iso-flow conditions based on environmental or patient temperature changes. Thus, the direction of change in response to inspiration and exhalation may be consistent throughout the different temperature ranges potentially encountered by the patient Pt. Inspiration is reflected by a cooling of the sensor starting at t1 and t2 and ending at t3 and t4, and the start of exhalation is reflected by the returning of the signal to its baseline starting at t3 and t4 and ending at t5 and t6, which reflects the end of exhalation.

In FIG. 7, another embodiment of the present invention is described in which temperature sensing element S1 is placed in a flow conduit 206 in or near the airway TA, which allows inspiratory and expiratory flow to pass through. The conduit 206 may be positioned on the ventilation catheter 25 such that the proximal and distal openings of the conduit 206 are in line with the axis of the tracheal or airway airflow 200. A ventilation gas flow lumen 210 may pass through the ventilation tube 25. The conduit 206 of known cross sectional area then can be used to correlate the sensor signal to airflow rate, based on for example known correlation factors and look up tables. For example, the slope of the sensor signal a/b, as shown in FIG. 7B, divided by the cross sectional area of the conduit may give a value in units of [(volts*[cross sectional area]^2)/time] which can be correlated to liters per minute based on a correlation factor of volts to distance. The resultant value is the flow rate Q(c) though the conduit 206. Q(c) can then be correlated to the flow rate in the trachea or airway by a correlation factor correlating the conduit size with the tracheal lumen size or airway size. Therefore, this may provide a breathing waveform of the inspiratory and expiratory breathing curves useful in deriving the patient's spontaneous inspiratory and expiratory flow rates and breathing volumes. Inspiratory and expiratory flow rate can be useful in determining the breathing effort of the patient and titrating the ventilation therapeutic level to the needs of the patient. FIG. 7A shows a variation of FIG. 7 in which two sensors S1 and S2 are disposed in a channel wherein the channel is within the ventilation tube, and in which airway airflow passes through the channel and past the sensors S1 and S2 via a fenestration 102 or via the main lumen of the ventilation tube.

In FIG. 8, another embodiment of the present invention is described with a ventilation tube including two temperature sensing elements $T_1$ and $T_H$ arranged in a Wheatstone bridge circuit, where one element Th may be heated to a temperature above the maximum temperature anticipated in the trachea or airway. This may offset the bridge signal so that the direction of airflow is easier to determine. FIG. 8A shows a bridge circuit diagram W of the sensing system shown in FIG. 8, with $T_1$ and $T_H$ in the circuit with two balancing resistors Re. FIG. 8B shows the signal tracings from the sensors $T_1$ and $T_H$, with $T_H$ at a higher amplitude than that of $T_1$. Therefore, comparing the two signals together can determine inspiratory and expiratory phase regardless of ambient temperature.

FIG. 9 describes two temperature sensitive sensors, for example thermistors, arranged in a Wheatstone bridge configuration in which both thermistors may be heated to a temperature greater than that anticipated in the trachea or airway, for example to 130° F. surface temperature. FIG. 9A describes the signal of each sensor $T_{H1}$ and $T_{H2}$ before and after being heated at time $t_h$. FIG. 9B describes the bridge output signal at a high and low ambient temperature condition, before and after $T_{H1}$ and $T_{H2}$ are heated at time $t_h$. The output of the Wheatstone bridge during iso-flow conditions may be balanced, however, when flow occurs, and the signal may change in response to cooling. In this case cooling is represented by an increase in amplitude of the signal. An increase of the signal, or cooling, may occur in both inspiration and exhalation since the outside air and the lung air temperature may be less than 130° F. The phase of respiration can be detected by another means, such as predictive algorithms or other sensors, such as a pressure sensor. When the elements are heated at time $t_h$, as depicted by the arrow in FIGS. 9a and 9b, the signals of each element shift up (FIG. 9a). As can be seen in FIG. 9b, after the bridge circuit output rebalances from the heating of the elements (shown by the bounce after when the heater is turned on), the bridge circuit output signal may be the same characteristic when the ambient temperature is 20° C. or 50° C. Therefore, changing ambient temperature conditions may not affect the phase or characteristic of the signal. The sensors' surface, at 130° F., may compromise the tracheal wall tissue if there is prolonged contact, hence, a means to shut off the heating of the sensor may be provided if contact with the tissue is sensed. This would be detected by a certain characteristic signal response and frequency response of the sensor being in contact with a 98° F. object. In addition the sensor surfaces can be protected to avoid contact with the tracheal wall, for example with a guard or a shape of the catheter, as shown.

FIG. 10 describes a ventilation tube 25 that may include two temperature sensing elements T1, T2 and a heat source H located near the temperature sensing elements T1, T2. The heat source H may produce a temperature gradient 212 above the temperature which would be anticipated in the trachea or nasal or oral airway, for example 120° F., but below the temperature that would be irritating or damaging to the user's skin or airway tissue. Ideally the heat source is placed on a location of the ventilation tube that does not come into contact with the skin or airway tissue. The heat from the heat source is drawn to the sensing elements during inspiration. Therefore, the sensing elements T1, T2 may always register an increase in temperature during inspiration regardless of ambient temperature. As can be seen in the tracings of the signals from T1 and T2 shown in FIGS. 10A and 10B, the signals are similar when ambient temperature is above and below body temperature. The heater can alternatively be placed in between the elements or on either side of the elements and the signal interpreted accordingly. The elements can be independently operated or can be arranged in a Wheatstone bridge configuration as previously described. Phase shift between the signals, or a comparison between the signals can be used to obtain flow information.

FIG. 11 describes a variation on the embodiment described in FIG. 10 in which the two temperature sensitive elements T1, T2 are arranged in a Wheatstone bridge circuit that may correct for drift in the signals. The output signal of the bridge circuit, as shown in FIG. 11A may be differentiated to correct of offset and to obtain a signal that is in phase with the breathing flow curve. This overall arrangement may produce a consistent and normalized signal throughout different ambient temperature conditions. The heater H may include a protective spacer to insure that the heater does not come into contract with the tracheal, nasal or oral tissue for prolonged periods.

FIG. 12 describes a ventilation tube 25 that includes a single temperature sensing element T1 arranged in a modified Wheatstone bridge circuit W', shown in FIG. 12A. To prevent drift of the signal due to the variable conditions, auto-correction may be made by adjusting the input to an amplifier, where the adjustment is determined in software in the microprocessor μP, as shown in FIG. 12A. Alternately, the current of voltage supplied to the sensor may be periodically adjusted such that the DC component of the sensor output is held hear the center of the element's operating range. The DC component may be computed by low pass filtering the sensor output. When a DC offset correction is made, detection of airflow direction and speed may be momentarily suspended until the DC offset correction settles. FIG. 12B describes the output of the sensor shown in FIG. 12 without software or DC drift compensation, showing a floating signal. FIG. 12C describes the output of the circuit shown in FIG. 12A in which the signal has a steady offset without drift. FIG. 12D describes where the temperature sensing element described in FIG. 12 is heated to a temperature above that which would be anticipated in the trachea, for example to 120° F., and arranged in the modified bridge circuit described in FIG. 12E. In this configuration, drift is corrected by the bridge circuit, and the effect of changing ambient temperature conditions is negated by the heating of the element.

FIGS. 13 and 13A describe an embodiment in which the airway temperature and ambient temperature are monitored as part of a breath sensing system, and in which the airway temperature is used to determine spontaneous breathing airflow. If the ambient temperature is low, as shown by Tamb in FIG. 13, an increasing slope of the Taw signal implies expiratory phase and a decreasing slope implies inspiratory phase. If the ambient temperature is high, as shown in Tamb in FIG. 13A, the converse of FIG. 13 is true.

FIGS. 14A-14D describe an embodiment in which temperature sensing elements measure intra-airway temperature Taw, temperature at the point of gas entry to the patient, T1, and ambient temperature Tamb. Locations of the sensing elements are described in FIG. 14D. Comparison of these three temperature signals may provide information required to correlate the Taw signal to an inspiratory and expiratory flow signal. The Tamb signal may determine if inspiratory airflow is warmer or cooler than expiratory airflow, and the T1 signal may provide a comparison to Taw in order to compensate for drift and artifacts.

FIG. 15 describes another embodiment of the present invention in which a ventilation tube 25 comprises a gas delivery lumen 210 and a sensing lumen 208. FIG. 15A shows a detailed view of area B in FIG. 15. A thermal sensing element T1 is disposed in the sensing lumen or conduit 208. When the patient inhales or exhales, some airflow flows out of and into the sensing lumen 208 and past the sensing element T1. In this manner, the phases of breathing can be detected by the sensing element T1. The machine end of the sensing lumen 208 may optionally be open to atmosphere in order to enhance the amount of flow flowing through the sensing lumen 208 and past the sensing element T1. The temperature of the inspired air in the sensing lumen 208 should be slightly cooler than the temperature of the exhaled air and hence the resultant signal, T1 as shown in FIG. 15B, can be correlated to flow direction and the breath cycle. The sensing element can be heated or can be arranged in a bridge circuit as described in previous embodiments to compensate for drift and ambient temperature ranges.

FIG. 16 describes an option to the embodiment of FIG. 15 in which there are two temperature sensing elements, T1 and T2, placed in the sensing lumen 208. FIG. 16A shows a detailed view of area B in FIG. 16. The two signals from T1 and T2 may provide more information than just one element, and can be used to help determine the direction of flow. For example one element can possess different thermal properties compared to the other element to dampen or shift the resultant signal, so that the direction of flow can be determined by signal comparison. As can be seen in FIG. 16B, the signals from T1 and T2 are different in phase and amplitude. The signal differences can be used to correct for noise, drift and other artifacts, as well as determine air flow direction and airflow strength. As previously described one or both sensing elements can be heated or the elements can be arranged in a Wheatstone bridge circuit, to compensate for signal drift and/or negate the effect of changing ambient temperature conditions.

FIG. 17 describes an optional embodiment in which an array of thermal sensors S1, S2 and S3 are placed in the airway TA, in a sensing lumen 208 as described in FIG. 16, and in the gas delivery circuit 24. Optionally, the sensing lumen 208 can be open to ambient air AMB at or near the ventilator end of the system, in order to enhance spontaneous breathing air flow flowing through the sensing lumen. FIG. 17A describes a detailed view of area C in FIG. 17, indicating S1 placed in the airway of the patient, S2 placed in a sensing lumen 208 that is part of the ventilation tube 25. The resultant signals are described in FIG. 17B, which show that the signal from S1 is the strongest spontaneous breathing signal, S2 is a weaker spontaneous breathing signal, and the signal form S3 shows both the ventilation delivery as well as spontaneous breathing when the ventilator is not active. Information from these three sensors can be used to understand what the breathing and ventilator conditions are at any given time, and can be used to cross check each other. In the case in which the ventilation parameters create entrainment of ambient air that is induced by ventilation gas delivered through and exiting the gas delivery channel 210, the airway sensor S1 can be used to measure entrainment of ambient airflow. Again, the sensing elements can be heated or arranged in bridge circuits to compensate for ambient temperature conditions and drift.

FIG. 18 describes an embodiment of the invention in which a ventilation tube 25 includes a physical screen or barrier 214 separating two sensing elements S1 and S2. The screen 214 provides a dampening or phase shift between the signals from the two sensors S1 and S2. As air flows in one direction, for example, inspiration I, as shown in FIG. 18A, the signal strength of S1 is relatively strong and undampened, and the strength of S2 is relatively weak and dampened due to the dampening effect that the screen 214 has on airflow. When air flows in the direction of exhalation E, as shown in FIG. 18B, signal S2 is stronger and more responsive thus indicating expiratory phase. Temporal and amplitude differences in the signal can be used to determine the direction of airflow. These sensing elements can be temperature sensitive elements or may work on other principles such as pressure, sound, ultrasound, optical, or other.

Alternatively to FIG. 18, FIG. 19 describes a ventilation tube 25 in which the sensors S1 and S2 are separated by the tube itself, achieving a similar result as described in the graphs shown in FIGS. 19A and 19B.

In another embodiment of the present invention, FIG. 20 describes a ventilation tube 25, which includes both a temperature sensing element T1 and a pressure sensor or pressure sensing port P1, in order to obtain both an airflow signal Q and a tracheal pressure signal P1 as shown in FIG. 20A. Optionally, two temperature sensing elements T1 and T2 can be used in a sensing array or Wheatstone bridge arrangement as previously described. The pressure signal P1 can be used to determine breath phase as well as airway pressure (i.e., negative pressure corresponding to inspiration), and this breath phase detection can be used to calibrate the temperature element signal to the correct phase of breathing, so inspiratory airflow can be distinguished reliably from expiratory airflow, regardless of the prevailing temperature conditions and ambient conditions. If two temperature sensing elements are used, they can be combined in a circuit as previously described and differentiated to normalize the signal and compensate for drift. The information obtained by this sensing configuration can be used to determine lung compliance, airway resistance and an estimate of work of breathing by establishing a correlation between airway pressure and pleural pressure. The flow signal can also be used to determine inspiratory and expiratory effort and depth of breathing, which can be used to titrate the ventilation parameters to the needs of the patient in a biofeedback loop.

FIG. 21 describes another embodiment of the present invention in which the sensor S1 is flushed with flow exiting a flush port 220. FIG. 21a describes a detailed view of area E in FIG. 21, and shows a dedicated flush lumen 224 leading to the flush port 220.

FIG. 22 describes an alternative embodiment wherein the flush lumen 224 branches off of the main gas delivery lumen 210.

FIG. 23A describes an alternative embodiment in which the sensor and flush port are located on the inferior or anterior side of the ventilation tube, as opposed to the superior or posterior side. In addition, the sensor and flush port can be located on the lateral side, on the superior side, or on the inferior side of the ventilation tube (not shown). FIG. 23B describes an alternate configuration in which the flush port is located distal to the sensor and flushes in the reverse direction back at the sensor.

FIGS. 24A-24C describe alternate pressure or flow delivery profiles of the flushing media being delivered, for example continuous as in FIG. 24A, pulsatile as in FIG. 24C, intermittent as in FIG. 24B, or as needed when the sensor signal appears degraded. The flush media can be a respiratory gas such as oxygen, a therapeutic gas such as helium, humidified air, or a liquid such as saline, a mucolytic or a medicant.

FIGS. 25-25D describe an embodiment where a ventilation and breath sensing system includes a ventilator V, a gas delivery circuit 24, and a ventilation catheter 26 or ventilation tube 25 placed into an outer sleeve 28, 29 such as a tracheostomy tube or stomal sleeve, or airway guide such as a nasal sleeve or oral sleeve. FIG. 25 describes the overall system of this embodiment. FIG. 25A describes the ventilation tube. FIG. 25B describes the outer sleeve. FIG. 25C describes a cross sectional view through line C-C of FIG. 25 showing the pressure sensor P1 and thermal airflow sensor T1 and optional inspiratory valve 122. FIG. 25D describes a cross sectional view through line D-D of FIG. 25 showing the optional heat moisture exchanger 118 and bacterial filter 120. In addition to the patient inspiring spontaneously through the upper airway 200, the patient can also inspire from ambient air through the annular space between the ventilation catheter 26 or ventilation tube 25 and the outer sleeve and optionally through an inspiratory flow valve 122 and/or outer cannula breathing flow port 116. A tracheostomy tube neck flange 112 and/or a tracheostomy tube ventilation circuit connector 111 may be provided. A heat moisture exchanger 118 and a bacterial filter 120 are optionally provided in the annular space. Further, breath sensors can optionally be placed in the annular space, for example a thermal sensor T1 for detecting inspiratory flow and/or expiratory flow and a pressure sensor or sensing port P1 for measuring airway pressure.

The embodiments described above are exemplary and certain features can be combined. The sensors can be disposed on the ventilation catheter or ventilation tube or on an outer sleeve, and can be placed on the anterior, inferior, lateral, superior, or posterior sides or combinations thereof. The ventilation catheter or tube can be inserted directly into a stoma or airway, or into a tracheal sleeve, such as a tracheostomy tube, stoma guide or stent, or an airway sleeve such as a nasal or oral guide. The ventilation catheter or tube and the sleeve, if used, can be comprised of a variety of shapes and curves, and can include protective features to protect the sensors and centering features to center the catheter or tube in the airway. In the case that the ventilation catheter or tube is placed directly in through the stoma, shapes and protective features are employed to prevent the sensing element from contacting the tracheal wall and signal disruption. In the case that the ventilation catheter or tube is placed into a sleeve such as a tracheostomy tube, the sensors can be inside the tracheostomy tube for protection. Typically the tracheostomy tube is fenestrated so that there is adequate airflow past the sensors during inspiration and exhalation.

In addition, while the embodiments have been described typically in conjunction with a transtracheal interface, they can also be endrotracheal, oral, nasal, or face or nose masks interfaces. For example, the patient interface can be a transnasal or trans-oral catheter entering the airway from the nose or mouth. Or, the patient interface can be a open oral or open nasal cannula or catheter, in which the distal end of the cannula or catheter can be adapted to be positioned slightly inside the oral or nasal cavity, or at the entrance to the oral or nasal airway, or outside of the oral or nasal airway directed at the entrance to the airway. Or, the patient interface can be an oral and/or nasal mask. In the case of the more invasive interfaces or catheters, the tip of the catheter can be located in any of the lung airways. In the case of the less invasive interfaces, the tip of the catheter can penetrate the airway barely. In the case of non-invasive interfaces, the tip of the tube, cannula, or mask can be outside of the airway.

The ventilation tube or tracheostomy tube may comprise an inflatable and deflatable cuff, and the sensors or sensing lumens can be provided on the distal and proximal side of the cuff (not shown) to sense pressures or flows on both sides of the cuff, to provide an indication of the resistance being caused by the cuff. For example if the cuff is not completely deflated, the data from the two sensors or sensing ports will register a higher than expected pressure drop, indicating to the user that the cuff is not fully deflated for upper airway breathing, or the tube is too big for that particular patient or situation. Optionally the two sensors can be used to monitor cuff inflation if and when closed ventilation is being applied to the patient.

The thermal sensing elements described are typically thermistor elements, however can be thermally response polymers, or other thermally responsive materials. They can be negative coefficient or positive coefficient, or both.

The ventilation therapy described in the embodiments can be augmented ventilation in which the patient is receiving a portion of their tidal volume from the ventilator, can be open ventilation in which the patient is spontaneously breathing through their upper airway, or can be closed or partially closed ventilation in which the patient's effort triggers the ventilator. The delivery circuit can be a single limb breathing circuit or dual limb breathing circuit. The invention can be applied to respiratory insufficiencies such as COPD, forms of neuromuscular weakness and paralysis, or airway disorders such as sleep apnea therapy. The therapy can be applied to adults, pediatrics and neonates.

The information made available by the breath sensors described herein can be used to synchronize ventilator functions to the patient's breath cycle, but can also be used to automatically adjust ventilator output and can be used for diagnostic purposes and trending analysis. The ventilator functions being controlled by the sensor information can be (1) delivery timing of gas from the ventilator, for example at a certain point of the inspiratory phase, a certain point of the expiratory phase, etc.; (2) amplitude, speed or waveform shape of ventilator output; or (3) frequency of ventilator output; or (4) composition of ventilator output, or combinations of the above.

Typical dimensions of the embodiments, assuming a transtracheal catheter interface are listed below. Dimensions for other interfaces, such as oral or nasal catheters or cannula include the requisite dimensional adjustments:

1. Ventilation tube or catheter: 2 mm OD to 12 mm OD, preferably 3-5 mm, 0.5-6 mm ID, preferably 1-3 mm ID. Insertion length 10 mm to 150 mm, preferably 30-100 mm. Curved such that there is a distal straight section aligned with the lumen of the trachea. Durometer 40-80 Shore D.

2. Single limb ventilation circuit: 4 mm OD to 12 mm OD, preferably 5-8 mm OD, 24-48 inches in length.

3. Gas delivery lumen: 0.5-6 mm ID, preferably 1-3 mm ID

4. Sensing lumen: 0.25-3 mm ID, preferably 0.5-1.75 mm and most preferably 0.75-1.5 mm.

5. Thermal sensing element: 0.25 mm-1.5 mm cross sectional dimension, 1-5 mm length. The thermal sensing element can also be a circumferential band around the diameter of the ventilation tube, or a strip of material.

6. Flow conduit: 0.5-2.0 mm ID, preferably 1-1.5 mm ID.

7. Flush port: 0.25-2 mm width or length or diameter.

8. Flush lumen: 0.2 mm-1.0 mm, preferably 0.25-0.5 mm.

| List of Reference Symbols: | |
|---|---|
| Amb: | Ambient |
| Amp: | Amplifier of Wheatstone bridge output |
| A/D: | Analog to digital comparator |
| D/A: | Digital to analog comparator |
| E: | Expiratory |
| H: | Heater |
| I: | Inspiratory |
| L: | Lung(s) |
| P1, P2, P3: | pressure transducer 1, 2 and 3 |
| PS: | Power supply for Wheatstone bridge |
| Pt: | Patient |
| Pf: | Flush pressure level |
| Q: | Tracheal airflow trace |
| R: | Respiration trace |
| R1, R2, R3: | Bridge circuit resistors |
| Re: | Resistor in Wheatstone bridge |

-continued

List of Reference Symbols:

| | |
|---|---|
| S: | Breath sensor signal trace |
| S1, S2, S3: | Sensing elements |
| TA: | Tracheal airway |
| t: | Time |
| Tp: | Proximal thermal sensing element |
| Td: | Distal thermal sensing element |
| TH: | Heated sensing element |
| T1: | Thermal sensing element one |
| T2: | Thermal sensing element two |
| TH1: | Heated sensing element one |
| TH2: | Heated sensing element two |
| Taw: | Airway temperature |
| Tamb: | Ambient temperature |
| uP: | Microprocessor |
| V: | Ventilator |
| V1, V2: | Voltage |
| V+: | Output voltage from bridge circuit |
| V−: | Input voltage to bridge output amplifier |
| W: | Wheatstone bridge circuit |
| W': | Modified Wheatstone bridge circuit |
| 10: | Processor |
| 20: | Ventilator control unit |
| 21: | Ventilation gas delivery circuit, dual limb |
| 23: | Ventilation circuit pressure tap |
| 24: | Ventilation gas delivery circuit, single limb |
| 25: | Ventilation tube |
| 26: | Ventilation catheter |
| 28: | Tracheostomy tube outer cannula |
| 29: | Stoma sleeve, guide or stent |
| 52: | Ventilator gas delivery pressure tracing |
| 58: | Patient spontaneous respiration curve |
| 60: | Chest impedance wires |
| 62: | Chest impedance band |
| 63: | Patient inspiratory effort |
| 66: | Patient exhalation tracheal flow/pressure curve |
| 77: | Chest impedance tracing |
| 102: | Ventilation catheter fenestration(s) |
| 111: | Tracheostomy tube ventilation circuit connector |
| 112: | Tracheostomy tube neck flange |
| 116: | Ventilation catheter - outer cannula breathing flow port |
| 118: | Ventilation catheter - outer cannula heat moisture exchange |
| 120: | Ventilation catheter - outer cannula filter |
| 122: | Inspiratory valve |
| 200: | Inspiratory flow |
| 202: | Expiratory flow |
| 204: | Ventilator gas flow |
| 206: | Sensor flow conduit |
| 208: | Sensing lumen |
| 210: | Ventilator gas flow lumen |
| 212: | Temperature gradient |
| 214: | Sensor physical barrier |
| 220: | Sensor flush port |
| 224: | Flush lumen |

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

What is claimed is:

1. An apparatus for sensing respiration and synchronizing a ventilator to the respiration of a patient, the apparatus comprising:
    at least three thermal breath sensors;
    wherein a first thermal breath sensor measures temperature in an airway of the patient, a second thermal breath sensor measures temperature at or near the opening of an airway of the patient, and a third thermal breath sensor measures ambient temperature;
    wherein signals from the first thermal breath sensor and the second thermal breath sensor are initially compared to a signal from the third thermal breath sensor to determine if inspired ambient air should be warmer or cooler than body temperature, and wherein the initial signal comparison defines an inspiratory phase and an expiratory phase associated with the signals from the first thermal breath sensor and the second thermal breath sensor; and
    wherein the signals from the first thermal breath sensor and the second thermal breath sensor are subsequently compared to each other to compensate for drift and artifacts, and wherein the subsequent signal comparison is used to determine true patterns, phases and timing of the patient's respiration.

2. The apparatus of claim 1, wherein the at least three thermal breath sensors have attributes selected from the group consisting of: (1) the first thermal breath sensor and the second thermal breath sensor are joined in a bridge circuit; (2) at least one of the first thermal breath sensor and the second thermal breath sensor are heated to maintain a desired baseline temperature compared to ambient temperature; (3) at least one of the first thermal breath sensor and the second thermal breath sensor are heated using a heat source decoupled from the at least one of the first thermal breath sensor and the second thermal breath sensor; and (4) combinations thereof.

3. The apparatus of claim 1, wherein the at least three thermal breath sensors have configurations selected from the group consisting of: (1) the first thermal breath sensor and the second thermal breath sensor are in communication with spontaneous airflow and are joined in a bridge circuit, and the third thermal breath sensor is not in communication with spontaneous airflow and is a reference sensor; (2) at least one of the at least three thermal breath sensors is positioned in a conduit that is in communication with spontaneous airflow, wherein the cross-section of the conduit and sensor signal are used to determine a volumetric flow rate; (3) the first thermal breath sensor and the second thermal breath sensor are separated by a barrier to create a directionally biased signal response phase shift between the signals of the first thermal breath sensor and the second thermal breath sensor, wherein the phase shift directionality is used to determine the direction of airflow and the phase of respiration; and (4) combinations thereof.

4. The apparatus of claim 1, wherein a DC shift of a signal of at least one of the at least three thermal breath sensors is controlled by (1) continually adjusting a source voltage or (2) auto-zeroing through a software feedback loop.

5. The apparatus of claim 1, wherein the at least three thermal breath sensors are selected from the group consisting of: thermistors; polymer based thermally responsive materials; thermally responsive materials shaped like a bead, strip or ring; and combinations thereof.

6. The apparatus of claim 1, wherein a signal from one or both of the first thermal breath sensor and the second thermal breath sensor is correlated to flow, and the flow is correlated to depth of breathing, inspiratory effort, inspiratory and expiratory flow, inspiratory and expiratory volume, and patient respiratory status.

* * * * *